(12) United States Patent
Guevremont et al.

(10) Patent No.: US 6,998,608 B2
(45) Date of Patent: *Feb. 14, 2006

(54) FAIMS WITH NON-DESTRUCTIVE DETECTION OF SELECTIVELY TRANSMITTED IONS

(75) Inventors: Roger Guevremont, Ottawa (CA); Randy Purves, Orleans (CA); David Barnett, Orleans (CA)

(73) Assignee: Ionalytics Corporation, Ottawa (CA)

( * ) Notice: Subject to any disclaimer, the term of this patent is extended or adjusted under 35 U.S.C. 154(b) by 140 days.

This patent is subject to a terminal disclaimer.

(21) Appl. No.: 10/338,858

(22) Filed: Jan. 9, 2003

(65) Prior Publication Data

US 2003/0150986 A1 Aug. 14, 2003

Related U.S. Application Data

(60) Provisional application No. 60/354,711, filed on Feb. 8, 2002.

(51) Int. Cl.
*B01D 59/44* (2006.01)
*H01J 49/00* (2006.01)
*H01J 49/40* (2006.01)

(52) U.S. Cl. .................. 250/288; 250/283; 250/282; 250/293; 250/292

(58) Field of Classification Search .............. 250/288, 250/283, 282, 293, 292, 287, 423 R, 281
See application file for complete search history.

(56) References Cited

U.S. PATENT DOCUMENTS

| | | | |
|---|---|---|---|
| 3,668,383 A | 6/1972 | Carroll | |
| 4,429,228 A | * 1/1984 | Anderson | 250/374 |
| 5,338,931 A | * 8/1994 | Spangler et al. | 250/287 |
| 5,420,424 A | 5/1995 | Carnahan et al. | |
| 5,905,258 A | 5/1999 | Clemmer et al. | |
| 5,945,790 A | * 8/1999 | Schaefer | 315/335 |
| 5,968,837 A | * 10/1999 | Doring et al. | 436/173 |
| 6,124,592 A | * 9/2000 | Spangler | 250/287 |
| 6,320,388 B1 | * 11/2001 | Sun et al. | 324/464 |
| 6,504,149 B2 | 1/2003 | Guevremont et al. | |
| 6,509,562 B1 | 1/2003 | Yang et al. | |
| 6,512,224 B1 | 1/2003 | Miller et al. | |
| 6,621,077 B1 | 9/2003 | Guevremont et al. | |
| 6,627,878 B1 | 9/2003 | Machlinski et al. | |
| 6,639,212 B1 | 10/2003 | Guevremont et al. | |
| 6,653,627 B2 | 11/2003 | Guevremont et al. | |
| 2003/0150984 A1 | 8/2003 | Guevremont et al. | |
| 2003/0150987 A1 | * 8/2003 | Guevremont et al. | 250/287 |

FOREIGN PATENT DOCUMENTS

| | | |
|---|---|---|
| WO | WO 01/69217 A2 | 9/2001 |
| WO | WO 01/69219 A2 | 9/2001 |

OTHER PUBLICATIONS

Carr et al., "Plasma Chromatography", Plenum Press (1984), NY, USA.

(Continued)

*Primary Examiner*—John R. Lee
*Assistant Examiner*—Kalimah Fernandez
(74) *Attorney, Agent, or Firm*—Freedman & Associates

(57) ABSTRACT

Disclosed is a high field asymmetric waveform ion mobility spectrometer (FAIMS) with optical based detection of selectively transmitted ions. Light from a light source is directed through an optical port in an electrode of the FAIMS. A light detector is provided for receiving light that is one of transmitted and scattered by the selectively transmitted ions within the FAIMS.

33 Claims, 14 Drawing Sheets

OTHER PUBLICATIONS

Baklanov et al., "Resonant Light Absorption by the Ordered Structures of Ions Stored in a Trap", Applied Physics B, 39, pp. 179–181, Springer–Verlag (1986).

Diedrich et al., "Nonclassical Radiation of a Single Stored Ion", Physical Review Letters, vol. 58, No. 3, pp. 203–206, The American Physical Society (Jan. 19, 1987).

Diedrich et al., "Observation of a Phase Transition of Stored Laser–Cooled Ions", Physical Review Letters, vol. 59, No. 26, pp. 2931–2934, The American Physical Society (Dec. 28, 1987).

Mason et al., "Transport Properties of Ions in Gases", Wiley (1988), NY, USA.

Buryakov et al., "A New Method of Separation of Multi-Atomic Ions by Mobility at Atmospheric Pressure using a High–Frequency Amplitude–Asymmetric Strong Electric Field", Int. J. Mass Spectrom. Ion Processes, No. 128, pp. 143–148, Elsevier Science Publishers B.V. (1993).

Eiceman et al., "Ion Mobility Spectrometry", (1994), CRC Press, FL, USA.

Carnahan et al., "Field Ion Spectrometry—A New Analytical Technology for Trace Gas Analysis", Proceedings of the 41st Annual ISA Analysis Division Symposium, paper #96–009, pp. 87–95, (1996), Farmingham, MA, USA.

Riegner et al., "Qualitative Evaluation of Field Ion Spectrometry for Chemical Warfare Agent Detection", Proceedings of the 45th ASMS Conference on Mass Spectrometry and Allied Topics, pp. 473, (1997), Palm Springs, CA, USA.

Purves et al., "Mass Spectrometric Characterization of a High–Field Asymmetric Waveform Ion Mobility Spectrometer", Review of Scientific Instruments, vol. 69, No. 12, pp. 4094–4105, American Institute of Physics (Dec. 1998).

Krylov, "A Method of Reducing Diffusion Losses in a Drift Spectrometer", Tech. Phys., vol. 44, No. 1, pp. 113–116, American Institute of Physics (1999).

Spangler, "Fundamental Considerations for the Application of Miniature Ion Mobility Spectrometry to Field Analytical Applications", Field Analytical Chemistry and Technology, 4, pp. 255–267 (2000), USA.

Eiceman et al., "Monitoring Volatile Organic Compounds in Ambient Air Anside and Outside Buildings with the use of a Radio–Frequency–Based Ion–Mobility Analyzer with a Micromachined Drift Tube", Field Analytical Chemistry and Technology, 4, pp. 297–308 (2000), USA.

Miller et al., "A Novel Micromachined High–Field Asymmetric Waveform–Ion Mobility Spectrometer", Sensors and Actuators B Chemical, 67, pp. 300–306, Elsevier Science S.A. (2000).

Miller et al., "A MEMS Radio–Frequency Ion Mobility Spectrometer for Chemical Vapor Detection", Sensors and Actuators A Physical, 91, pp. 307–318, Elsevier Science S.A. (2000).

Eiceman et al., "Miniature Radio–Frequency Mobility Analyzer as a Gas Chromatographic Detector for Oxygen–Containing Volatile Organic Compounds, Pheromones and other Insect Attractants", Journal of Chromatography A, 917, pp. 205–217, Elsevier Science B.V. (2001).

Buryakov et al., "Detection of Explosive Vapors in the Air Using an Ion Drift Nonlinearity Spectrometer", Journal of Analytical Chemistry, vol. 56, No. 4, pp. 336–240 (2001).

Spangler et al., "Application of Mobility Theory to the Interpretation of Data Generated by Linear and RF Excited Ion Mobility Spectrometers", International Journal of Mass Spectrometry, 12017, pp. 1–10, Elsevier Science B.V. (2002).

* cited by examiner

FAIMS WITH NON-DESTRUCTIVE DETECTION OF SELECTIVELY TRANSMITTED IONS

This application claims the benefit of U.S. Provisional Application No. 60/354,711 filed Feb. 8, 2002.

FIELD OF THE INVENTION

The instant invention relates generally to high field asymmetric waveform ion mobility spectrometry (FAIMS), more particularly the instant invention relates to an apparatus and method for non-destructive detection of ions separated by FAIMS.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. The drift velocity of an ion is proportional to the applied electric field strength at low electric field strength, for example 200 V/cm, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, N.Y., 1988) teach that at high electric field strength, for instance fields stronger than approximately 5,000 V/cm, the ion drift velocity is no longer directly proportional to the applied electric field, and K is better represented by $K_h$, a non-constant high field mobility term. The dependence of $K_h$ on the applied electric field has been the basis for the development of high field asymmetric waveform ion mobility spectrometry (FAIMS). Ions are separated in FAIMS on the basis of a difference in the mobility of an ion at high field strength, $K_h$, relative to the mobility of the ion at low field strength, K. In other words, the ions are separated due to the compound dependent behavior of $K_h$ as a function of the applied electric field strength.

In general, a device for separating ions according to the FAIMS principle has an analyzer region that is defined by a space between first and second spaced-apart electrodes. Often, the first electrode is maintained at ground potential while the second electrode has an asymmetric waveform V(t) applied to it. The asymmetric waveform V(t) is composed of a repeating pattern including a high voltage component, $V_h$, lasting for a short period of time $t_h$ and a lower voltage component, $V_l$, of opposite polarity, lasting a longer period of time $t_l$. The waveform is synthesized such that the integrated voltage-time product, and thus the field-time product, applied to the second electrode during each complete cycle of the waveform is zero, for instance $V_h t_h + V_l t_l = 0$; for example +2000 V for 10 $\mu$s followed by −1000 V for 20 $\mu$s. The peak voltage during the shorter, high voltage portion of the waveform is called the "dispersion voltage" or DV.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform an ion moves with a y-axis velocity component given by $v_h = K_h E_h$, where $E_h$ is the applied field, and $K_h$ is the high field ion mobility under operating electric field, pressure and temperature conditions. The distance traveled by the ion during the high voltage portion of the waveform is given by $d_h = v_h t_h = K_h E_h t_h$, where $t_h$ is the time period of the applied high voltage. During the longer duration, opposite polarity, low voltage portion of the asymmetric waveform, the y-axis velocity component of the ion is $v_l = K E_l$, where K is the low field ion mobility under ambient pressure and temperature conditions. The distance traveled is $d_l = v_l t_l = K E_l t_l$. Since the asymmetric waveform ensures that $(V_h t_h) + (V_l t_l) = 0$, the field-time products $E_h t_h$ and $E_l t_l$ are equal in magnitude. Thus, if $K_h$ and K are identical, $d_h$ and $d_l$ are equal, and the ion is returned to its original position along the y-axis during the negative cycle of the waveform. If at $E_h$ the mobility $K_h > K$, the ion experiences a net displacement from its original position relative to the y-axis. For example, if a positive ion travels farther during the positive portion of the waveform, for instance $d_h > d_l$, then the ion migrates away from the second electrode and eventually will be neutralized at the first electrode.

In order to reverse the transverse drift of the positive ion in the above example, a constant negative dc voltage called the "compensation voltage" or CV can be applied to the second electrode. This dc voltage prevents the ion from migrating toward either the second or the first electrode. If ions derived from two compounds respond differently to the applied high strength electric fields, the ratio of $K_h$ to K may be different for each compound. Consequently, the magnitude of the CV that is necessary to prevent the drift of the ion toward either electrode is also different for each compound. Thus, when a mixture including several species of ions, each with a unique $K_h/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

U.S. Pat. No. 5,420,424, issued to Carnahan and Tarassov on May 30, 1995, teaches a FAIMS device having cylindrical electrode geometry and electrometric ion detection, the contents of which are incorporated herein by reference. The FAIMS analyzer region is defined by an annular space between inner and outer cylindrical electrodes. In use, ions that are to be separated are entrained into a flow of a carrier gas and are carried into the analyzer region via an ion inlet orifice. Once inside the analyzer region, the ions become distributed all the way around the inner electrode as a result of the carrier gas flow and ion-ion repulsive forces. The ions are selectively transmitted within the analyzer region to an ion extraction region at an end of the analyzer region opposite the ion inlet end. In particular, a plurality of ion outlet orifices is provided around the circumference of the outer electrode for extracting the selectively transmitted ions from the ion extraction region for electrometric detection. Of course, the electrometric detectors provide a signal that is indicative of the total ion current arriving at the detector. Accordingly, the CV spectrum that is obtained using the Carnahan device does not include information relating to an identity of the selectively transmitted ions. It is a limitation of the Carnahan device that the peaks in the CV spectrum are highly susceptible to being assigned incorrectly. It is another limitation of the Carnahan device that the ions are consumed upon being detected at the electrometric detector. Accordingly, it is not possible to perform further analysis or separation of the ions, or to collect the ions for other uses.

Replacing the electrometric detector with a mass spectrometer detection system provides an opportunity to obtain additional experimental data relating to the identity of ions giving rise to the peaks in a CV spectrum. For instance, the mass-to-charge (m/z) ratio of ions that are selectively transmitted through the FAIMS at a particular combination of CV and DV can be measured. Additionally, replacing the mass spectrometer with a tandem mass spectrometer makes it possible to perform a full-fledged structural investigation of the selectively transmitted ions. Unfortunately, the selectively transmitted ions are difficult to extract from the analyzer region of the Carnahan device for subsequent detection by a mass spectrometer. In particular, the orifice plate of a mass spectrometer typically includes a single small sampling orifice for receiving ions for introduction into the mass spectrometer. This restriction is due to the fact that a mass spectrometer operates at a much lower pressure than the FAIMS analyzer. In general, the size of the sampling orifice into the mass spectrometer is limited by the efficiency of the mass spectrometer vacuum system. In principle, it is possible to align the sampling orifice of a mass spectrometer with a single opening in the FAIMS outer electrode of the Carnahan device; however, such a combination suffers from very low ion transmission efficiency and therefore poor detection limits. In particular, the Carnahan device does not allow the selectively transmitted ions to be concentrated for extraction through the single opening. Accordingly, only a small fraction of the selectively transmitted ions are extracted from the analyzer region, the vast majority of the selectively transmitted ions being neutralized eventually upon impact with an electrode surface.

Guevremont et al. describe the use of curved electrode bodies, for instance inner and outer cylindrical electrodes, for producing a two-dimensional atmospheric pressure ion focusing effect that results in higher ion transmission efficiencies than can be obtained using, for example, a FAIMS device having parallel plate electrodes. In particular, with the application of an appropriate combination of DV and CV an ion of interest is focused into a band-like region between the cylindrical electrodes as a result of the electric fields which change with radial distance. Focusing the ions of interest has the effect of reducing the number of ions of interest that are lost as a result of the ion suffering a collision with one of the inner and outer electrodes.

In WO 00/08455, the contents of which are incorporated herein by reference, Guevremont and Purves describe an improved tandem FAIMS/MS device, including a domed-FAIMS analyzer. In particular, the domed-FAIMS analyzer includes a cylindrical inner electrode having a curved surface terminus proximate the ion outlet orifice of the FAIMS analyzer region. The curved surface terminus is substantially continuous with the cylindrical shape of the inner electrode and is aligned co-axially with the ion outlet orifice. During use, the application of an asymmetric waveform to the inner electrode results in the normal ion-focusing behavior as described above, and in addition the ion-focusing action extends around the generally spherically shaped terminus of the inner electrode. This causes the selectively transmitted ions to be directed generally radially inwardly within the region that is proximate the terminus of the inner electrode. Several contradictory forces are acting on the ions in this region near the terminus of the inner electrode. The force of the carrier gas flow tends to influence the ions to travel towards the ion-outlet orifice, which advantageously also prevents the ions from migrating in a reverse direction, back towards the ion source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focusing effect of the electric fields of the FAIMS mechanism. This is an example of a three-dimensional atmospheric pressure ion trap, as described in greater detail by Guevremont and Purves in WO 00/08457, the contents of which are incorporated herein by reference.

Guevremont and Purves further disclose a near-trapping mode of operation for the above-mentioned tandem FAIMS/MS device, which achieves ion transmission from the domed-FAIMS to a mass spectrometer with high efficiency. Under near-trapping conditions, the ions that accumulate in the three-dimensional region of space near the spherical terminus of the inner electrode are caused to leak from this region, being pulled by a flow of gas towards the ion-outlet orifice. The ions that are extracted from this region do so as a narrow, approximately collimated beam, which is pulled by the gas flow through the ion-outlet orifice and into a smaller orifice leading into the vacuum system of the mass spectrometer. Accordingly, such tandem FAIMS/MS devices are highly sensitive instruments that are capable of detecting and identifying ions of interest at part-per-billion levels.

Unfortunately, the tandem FAIMS/MS arrangement suffers from a number of limitations. In particular, ions that are analyzed by mass spectrometry cannot be collected or analyzed further. Instead, the ions are neutralized upon impact with a detector element of the mass spectrometer, such as for instance an electron multiplier. Accordingly, it is not possible to analyze ions that are selectively transmitted by a first FAIMS device before they are provided to a second FAIMS device for additional separation in a tandem FAIMS/FAIMS arrangement. Similarly, it is not possible to provide the mass analyzed ions to a second detector for subsequent analysis by a complementary technique. Of course, analysis by a complementary technique provides an opportunity to probe characteristics of the ions other than mass-to-charge (m/z) ratio. For example, using an infrared analyzer to obtain the infrared spectrum of the ions provides information relating to the presence of specific chemical functional groups, etc.

Furthermore, the size of the sampling orifice into the mass spectrometer is very small, being limited by the efficiency of the mass spectrometer vacuum system. In order to transmit as many ions as possible from the FAIMS analyzer to the mass spectrometer, it is necessary to dispose the sampling orifice immediately adjacent to the ion-outlet orifice, such that widening of the ion beam as a result of ion diffusion and ion-ion repulsion is minimized. As will be obvious to one of skill in the art, the insertion of a non-destructive analyzer, such as for instance the above-mentioned infrared analyzer, intermediate the sampling orifice and the ion-outlet orifice results in a longer ion path to the mass spectrometer, which increases the amount of time for the ion beam to spread out radially. Of course, the efficiency of introducing ions into the mass spectrometer decreases as the cross section of the ion beam increases, and dilute samples may produce insufficient signal intensity for obtaining meaningful results.

It would be advantageous to provide a FAIMS apparatus including a detection system that overcomes the limitations of the prior art.

SUMMARY OF THE INVENTION

In accordance with an aspect of the invention there is provided an apparatus for separating ions in the gas phase, comprising: a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting a first type of ion along an average ion flow path within the analyzer region at a given combination of asymmetric waveform voltage and compensation voltage; and, an optical port disposed adjacent to a portion of the analyzer region other than a portion including an origin of the average ion flow path, the optical port formed of a light transmissive material other than a gas, which material is transmissive to light within a predetermined range of wavelengths for supporting the propagation of light having a wavelength within the predetermined range of wavelengths between the analyzer region and a region that is external to the analyzer region.

In accordance with another aspect of the invention there is provided an apparatus for separating ions in the gas phase, comprising: a high field asymmetric waveform ion mobility spectrometer comprising two electrodes defining an analyzer region therebetween, the two electrodes disposed in a spaced apart arrangement for allowing a gas flow to pass therebetween and for providing an electric field within the analyzer region resulting from the application of an asymmetric waveform voltage to at least one of the two electrodes and from the application of a compensation voltage to at least one of the two electrodes, for selectively transmitting a first type of ion along an average ion flow path within the analyzer region between an origin of the ion flow path and an ion outlet orifice of the analyzer region at a given combination of asymmetric waveform voltage and compensation voltage, whereby, in use, at least one of the asymmetric waveform voltage, the compensation voltage and the gas flow are adjustable, so as to confine some of the selectively transmitted ions within a 3-dimensional region of space within the analyzer region and adjacent to the ion outlet orifice; and, a first optical port disposed within a surface of one of the two electrodes and adjacent to the analyzer region at a point that is generally aligned with the 3-dimensional region of space within the analyzer region and adjacent to the ion outlet orifice, the first optical port formed of a material other than a gas, which material is transmissive to light within a predetermined range of wavelengths for propagating light including information relating to the selectively transmitted ions therethrough.

In accordance with still another aspect of the invention there is provided an apparatus for separating ions in the gas phase, comprising: a high field asymmetric waveform ion mobility spectrometer comprising two electrodes defining an analyzer region therebetween, the two electrodes disposed in a spaced apart arrangement for allowing a gas flow to pass therebetween and for providing an electric field within the analyzer region resulting from the application of an asymmetric waveform voltage to at least one of the two electrodes and from the application of a compensation voltage to at least one of the two electrodes, for selectively transmitting a first ion type in the analyzer region at a given combination of asymmetric waveform voltage and compensation voltage, whereby, in use, at least one of the asymmetric waveform voltage, the compensation voltage and the gas flow are adjustable, so as to confine some of the selectively transmitted ions within a 3-dimensional region of space within the analyzer region; a first optical port disposed within a surface of one of the two electrodes and adjacent to a portion of the analyzer region including the 3-dimensional region of space, the first optical port for propagating incident light along an optical path including the first optical port and the 3-dimensional region of space; and, a second optical port disposed within a surface of one of the two electrodes and adjacent to the portion of the analyzer region including the 3-dimensional region of space, the second optical port for propagating other light, resulting from the passage of the incident light through the 3-dimensional region of space, therethrough.

In accordance with yet another aspect of the invention there is provided an apparatus for separating ions in the gas phase, comprising: a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting a first ion type in the analyzer region at a given combination of asymmetric waveform voltage and compensation voltage; and, a probe signal generator for generating a probe signal which when applied to the selectively transmitted ions results in light including information relating to the selectively transmitted ions within the analyzer region.

In accordance with yet another aspect of the invention there is provided an apparatus for separating ions in the gas phase, comprising: a high field asymmetric waveform ion mobility spectrometer comprising two electrodes defining an analyzer region therebetween, the two electrodes disposed in a spaced apart arrangement for allowing a gas flow to pass therebetween and for providing an electric field within the analyzer region resulting from the application of an asymmetric waveform voltage to at least one of the two electrodes and from the application of a compensation voltage to at least one of the two electrodes, for selectively transmitting a first ion type in the analyzer region at a given combination of asymmetric waveform voltage and compensation voltage, whereby, in use, the asymmetric waveform voltage, the compensation voltage and the gas flow are adjustable, so as to confine some of the selectively transmitted ions within a 3-dimensional region of space within the analyzer region; a first optical port disposed within a surface of one of the two electrodes and adjacent to a portion of the analyzer region including the 3-dimensional region of space; and, a light source disposed external to the analyzer region and in optical communication with the first optical port for providing incident light having a wavelength within a predetermined range of wavelengths to the selectively transmitted ions within the 3-dimensional region of space.

In accordance with yet another aspect of the invention there is provided a method for separating ions in the gas phase, comprising the steps of: separating a mixture of ions including ions of a first type by selectively transmitting the ions of the first type through an analyzer region of a high field asymmetric waveform ion mobility spectrometer along an ion flow path between an ion inlet end of the analyzer region and an ion outlet end of the analyzer region; providing a stimulus to the selectively transmitted ions within at least a portion of the analyzer region for producing light including information relating to the selectively transmitted ions; and providing the light including information relating to the selectively transmitted ions to a light detector that is external to the analyzer region.

In accordance with yet another aspect of the invention there is provided a method for separating ions in the gas phase, comprising the steps of: separating a mixture of ions including ions of a first type by selectively transmitting the ions of a first type through an analyzer region of a high field asymmetric waveform ion mobility spectrometer along an ion flow path between an ion inlet of the analyzer region and an ion outlet of the analyzer region; confining some of the selectively transmitted ions within a 3-dimensional region of space adjacent to the ion outlet and within the analyzer region; directing incident light through the 3-dimensional region of space adjacent to the ion outlet and within the analyzer region for interacting with the selectively transmitted ions within the 3-dimensional region of space adjacent to the ion outlet and within the analyzer region; and, detecting light including information relating to the selectively transmitted ions resulting from an interaction between the incident light and the selectively transmitted ions confined within the 3-dimensional region of space adjacent to the ion outlet and within the analyzer region.

In accordance with yet another aspect of the invention there is provided a method for separating ions in the gas phase, comprising the steps of: effecting a first separation of the ions within a portion of an analyzer region between an ion inlet end of the analyzer region and a reaction portion of the analyzer region; affecting the ions within the reaction portion of the analyzer region so as to induce a structural change of the ions; and, effecting a second separation of the ions within a portion of an analyzer region between the reaction portion of the analyzer region and an ion outlet end of the analyzer region.

In accordance with yet another aspect of the invention there is provided an apparatus for separating ions in the gas phase, comprising: a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting a first type of ion along an average ion flow path within the analyzer region at a given combination of asymmetric waveform voltage and compensation voltage; an optical port disposed within a surface of one of the two electrodes and adjacent to an ion detecting portion of the analyzer region, the optical port for propagating light including information relating to the selectively transmitted ions therethrough; and, a light detector disposed external to the ion detecting portion of the analyzer region and in optical communication with the optical port for receiving the light including information relating to the selectively transmitted ions within the ion detecting portion and for providing an electrical signal relating to at least an intensity of the received light.

In accordance with yet another aspect of the invention there is provided an apparatus for separating ions in the gas phase, comprising: a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting a first type of ion along an average ion flow path within the analyzer region at a given combination of asymmetric waveform voltage and compensation voltage; and, an optical detector spaced apart from the average ion flow path for receiving light including information relating to the selectively transmitted ions within the average ion flow path so as to support a nondestructive determination of a characteristic of the selectively transmitted ions.

In accordance with yet another aspect of the invention there is provided a method for separating ions in the gas phase, comprising the steps of: separating a mixture of ions including ions of a first type by selectively transmitting the ions of the first type through an analyzer region of a high field asymmetric waveform ion mobility spectrometer along an average ion flow path between an ion inlet end of the analyzer region and an ion outlet end of the analyzer region; detecting light including information relating to the selectively transmitted ions using a light detector that is spaced apart from the average ion flow path; and, determining a characteristic of the selectively transmitted ions based on the detected light including information relating to the selectively transmitted ions.

BRIEF DESCRIPTION OF THE DRAWINGS

Exemplary embodiments of the invention will now be described in conjunction with the following drawings, in which similar reference numbers designate similar items:

FIG. 2b is a simplified end-on view of the FAIMS device of FIG. 2a;

FIG. 2c is an enlarged view of a first optical port configuration for use with the FAIMS device of FIG. 2a;

FIG. 2d is an enlarged view of a second optical port configuration for use with the FAIMS device of FIG. 2a;

FIG. 2e is an enlarged view of a third optical port configuration for use with the FAIMS device of FIG. 2a;

FIG. 2f is an enlarged view of a fourth optical port configuration for use with the FAIMS device of FIG. 2a;

FIG. 3b is a simplified end-on view of the FAIMS device of FIG. 3a;

FIG. 6b is a simplified end-on view of the FAIMS device of FIG. 6a;

FIG. 7b is a simplified end-on view of the FAIMS device of FIG. 7a;

DETAILED DESCRIPTION OF THE DRAWINGS

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein. Throughout the disclosure and in the claims that follow, the term "light including information relating to the selectively transmitted ions" is defined as one of scattered light, emitted light and transmitted incident light having a wavelength within one of the infrared, ultraviolet and visible regions of the electromagnetic spectrum, wherein one of the intensity, frequency, polarization and periodicity of intensity variation of the light is indicative of, for example, one of an ionic chemical structure, an ionic conformational state, an ionic density and a relative ionic density of the selectively transmitted ions within a FAIMS analyzer region. In addition, the term "average ion flow path" is defined as the net trajectory of the ions as a result of one of a carrier gas flow through the analyzer region and an electrical field gradient within the analyzer region, although the individual ions also experience an oscillatory motion between the electrodes as a result of the applied asymmetric waveform voltage.

Figure 1:
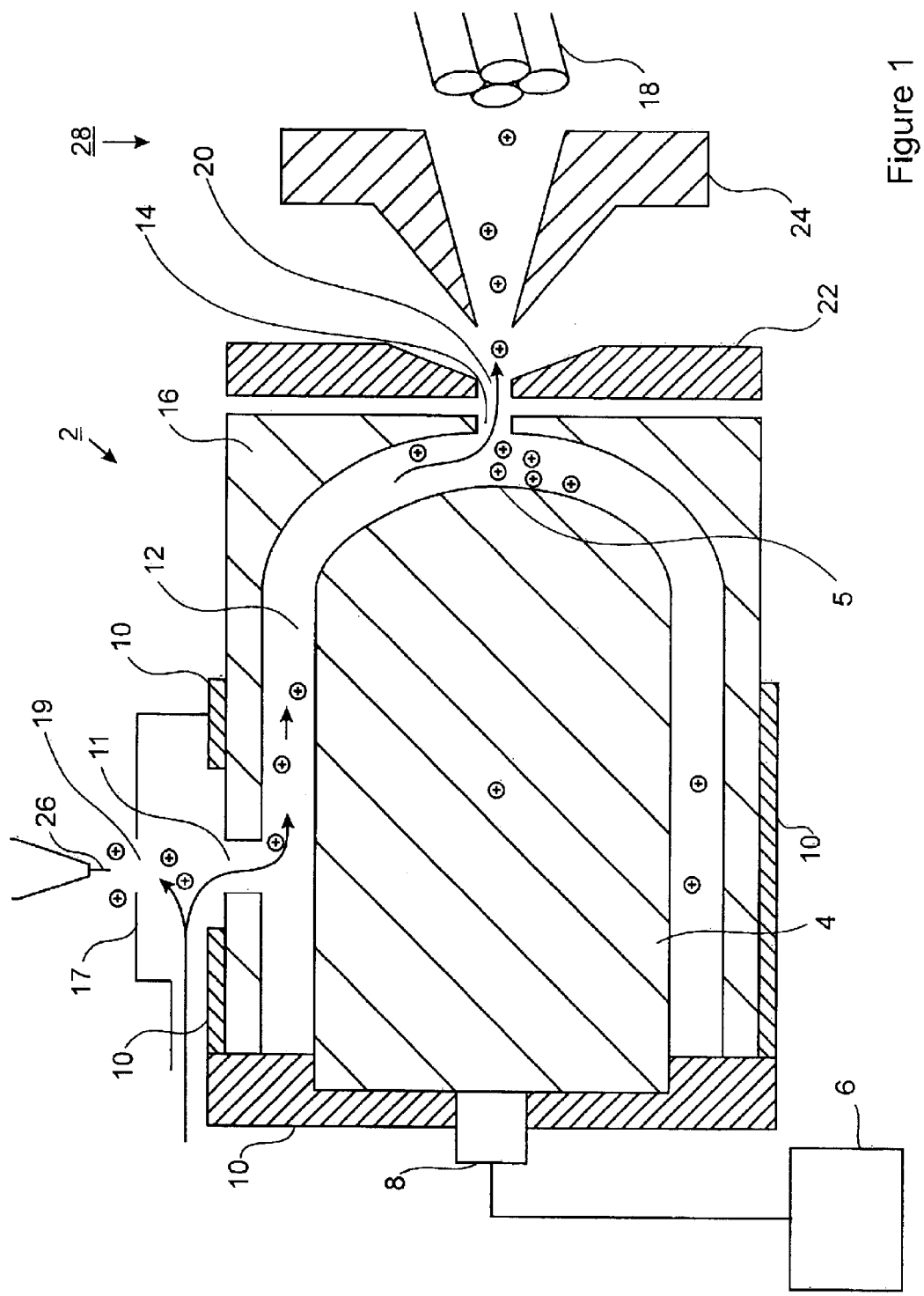
FIG. 1 is a simplified cross-sectional view of a tandem FAIMS/MS apparatus.

Referring to FIG. 1, shown is a simplified cross-sectional view of a tandem FAIMS/MS apparatus. In particular, a domed-FAIMS device 2 having cylindrical electrode geometry is shown in fluid communication with a mass spectrometer 28. The domed-FAIMS device 2 includes inner and outer cylindrical electrodes 4 and 16, respectively, which are supported by an electrically insulating material 10 in an overlapping, spaced-apart arrangement. The generally annular space between the inner electrode 4 and the outer electrode 16 defines a FAIMS analyzer region 12. The width of the analyzer region is approximately uniform around the circumference of the inner electrode 4, and extends around a curved surface terminus 5 of the inner electrode 4. An ion inlet orifice 11 is provided through the outer electrode 16 for introducing ions from an ion source 26 into the analyzer region 12. A flow of a carrier gas, which is represented in the figure by a series of closed-headed arrows, is provided within the analyzer region 12 to carry the ions toward an ion outlet orifice 14 located opposite the curved surface terminus 5 of the inner electrode 4. An orifice 19 within a curtain plate electrode 17 allows for the flow of a portion of the carrier gas in a direction that is counter-current to the direction in which the ions are traveling near the ion inlet 11, so as to desolvate the ions before they are introduced into the analyzer region 12. The inner electrode 4 is provided with an electrical contact 8 through the insulating material 10 for connection to a power supply 6 that during use is capable of applying a high voltage asymmetric waveform voltage (DV) and a low voltage dc compensation voltage (CV) to the inner FAIMS electrode 4.

The mass spectrometer 28 is disposed external to the FAIMS analyzer region 12, and includes an orifice plate 22 having an inlet orifice 20 extending therethrough. As will be apparent to one of skill in the art, the size of the inlet orifice 20 is typically very small, being limited by the efficiency of the mass spectrometer vacuum system. The inlet orifice 20 in the orifice plate 22 is aligned with the ion outlet orifice 14 of the domed-FAIMS device 2 such that ions being extracted through the ion outlet orifice 14 enter the mass spectrometer inlet orifice 20. Those ions that pass through the orifice 20 in the orifice plate 22 travel to a skimmer cone 24 within the differentially pumped region of the mass spectrometer 28, and are analyzed within a mass analyzer 18 on the basis of their mass-to-charge ratio. The mass spectrometer includes a not illustrated detector, such as for instance an electron multiplier, for providing an electrical signal that is proportional to a detected ion current.

During use, ions are produced at the ion source 26 from a suitable sample containing a species of interest. Typically, a mixture including a plurality of different ion types is produced when the sample is ionized. A potential gradient is used in order to accelerate the ions of the mixture away from the ion source 26, through the orifice 19 in the curtain plate electrode 17, and toward the ion inlet orifice 11, where the ions become entrained in the carrier gas flow and are carried into the FAIMS analyzer region 12. Once inside the FAIMS analyzer region 12, the ions are carried through an electric field that is formed within the FAIMS analyzer region 12 by the application of the DV and the CV to the inner FAIMS electrode 4 via the electrical contact 8. Ion separation occurs within the FAIMS analyzer region 12 on the basis of the high field mobility properties of the ions. Those ions of the mixture that have a stable trajectory for a particular combination of DV and CV are selectively transmitted through the FAIMS analyzer region 12, whilst other ions of the mixture collide with an electrode surface and are lost. Since the electric field also extends around the curved surface terminus 5, the selectively transmitted ions tend to be directed generally radially inwardly towards the ion outlet orifice 14. Near trapping conditions are created within the analyzer region 12 by adjusting at least one of the carrier gas flow rate, the carrier gas composition, the applied CV, the applied DV, the distance between the curved surface terminus 5 and the ion outlet orifice 14, the potential that is applied to the orifice plate 22, the temperature of the carrier gas and the pressure of the carrier gas. Under trapping conditions, which are created within the analyzer region 12 by adjusting at least one of the above-mentioned parameters to a different value, the selectively transmitted ions accumulate within a 3-dimensional region of space proximate the curved surface terminus 5. Under near-trapping conditions the ions also accumulate within the 3-dimensional region of space proximate the curved surface terminus 5, except that a lower ion density is achieved when operating under near-trapping conditions, since the ions are being continually extracted from the 3-dimensional region of space as an approximately collimated beam of ions. The extracted ions are carried by the carrier gas flow through the ion outlet orifice 14.

Figure 2A:
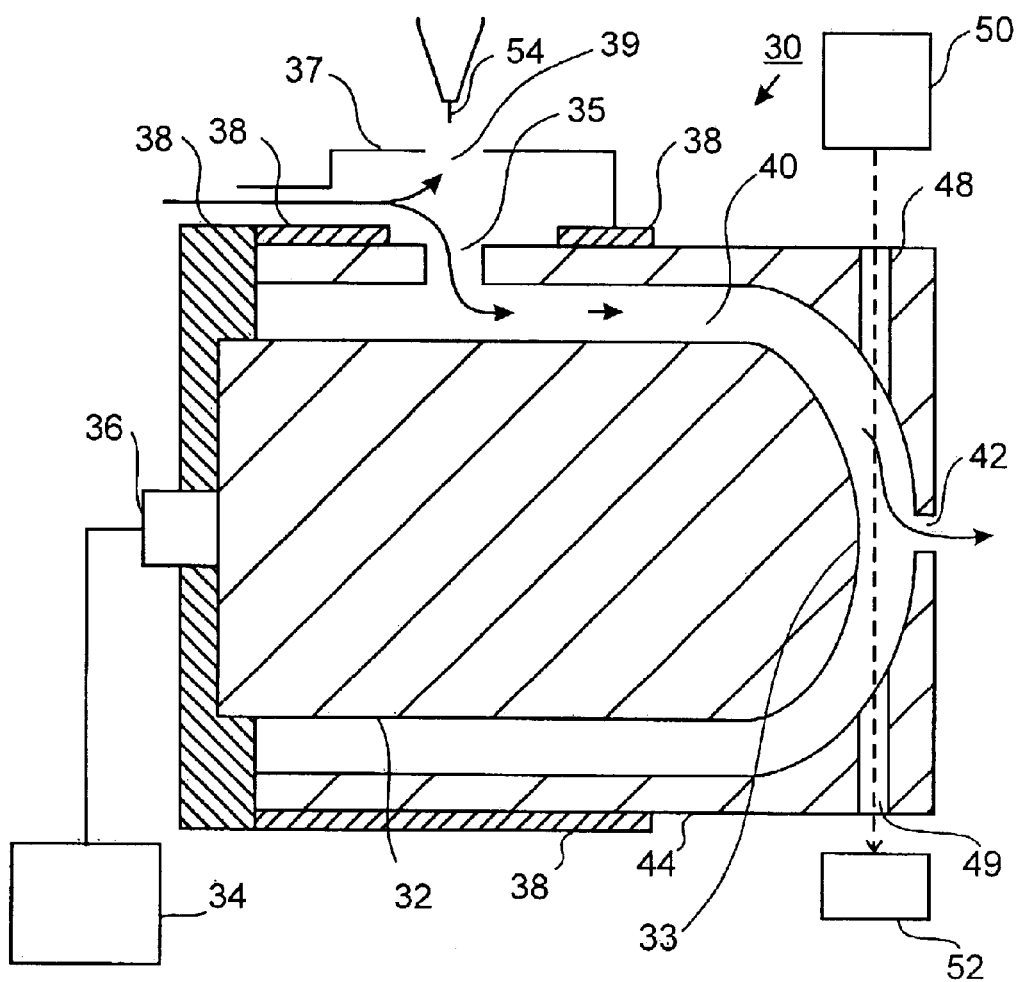
FIG. 2a is a side cross-sectional view of a FAIMS device according to a first embodiment of the instant invention.

Referring now to FIG. 2a, shown is a side cross-sectional view of a FAIMS device 30 according to a first embodiment of the instant invention. The FAIMS device 30, in the form of a domed-FAIMS device, includes inner and outer cylindrical electrodes 32 and 44, respectively, which are supported by an electrically insulating material 38 in an overlapping, spaced-apart arrangement. The generally annular space between the inner electrode 32 and the outer electrode 44 defines a FAIMS analyzer region 40. The width of the analyzer region is approximately uniform around the circumference of the inner electrode 32, and extends around a curved surface terminus 33 of the inner electrode 32. An ion inlet orifice 35 is provided through the outer electrode 44 for introducing ions from an ion source 54 into the analyzer region 40. A flow of a carrier gas, which is represented in the figure by a series of closed-headed arrows, is provided within the analyzer region 40 to carry the ions toward an ion outlet orifice 42 located opposite the curved surface terminus 33 of the inner electrode 32. An orifice 39 within a curtain plate electrode 37 allows for the flow of a portion of the carrier gas in a direction that is counter-current to the direction in which the ions are traveling near the ion inlet 35, so as to desolvate the ions before they are introduced into the analyzer region 40. The inner electrode 32 is provided with an electrical contact 36 through the insulating material 38 for connection to a power supply 34 that during use is capable of applying a high voltage asymmetric waveform voltage (DV) and a low voltage dc compensation voltage (CV) to the inner FAIMS electrode 32.

During use, ions are produced at the ion source 54 from a suitable sample containing a species of interest. Typically, a mixture including a plurality of different ion types is produced when the sample is ionized. A potential gradient is used in order to accelerate the ions of the mixture away from the ion source 54, through the orifice 39 in the curtain plate electrode 37, and toward the ion inlet orifice 35, where the ions become entrained in the carrier gas flow and are carried into the FAIMS analyzer region 40. Once inside the FAIMS analyzer region 40, the ions are carried through an electric field that is formed within the FAIMS analyzer region 40 by the application of the DV and the CV to the inner FAIMS electrode 32 via the electrical contact 36. Ion separation occurs within the FAIMS analyzer region 40 on the basis of the high field mobility properties of the ions. Those ions of the mixture that have a stable trajectory for a particular combination of DV and CV are selectively transmitted through the FAIMS analyzer region 40, whilst other ions of the mixture collide with an electrode surface and are lost. Since the electric field also extends around the curved surface terminus 33, the selectively transmitted ions tend to be directed generally radially inwardly towards the ion outlet orifice 42. Near trapping conditions are created within the analyzer region 40 by adjusting at least one of the carrier gas flow rate, the carrier gas composition, the applied CV, the applied DV, the distance between the curved surface terminus 33 and the ion outlet orifice 42, the temperature of the carrier gas and the pressure of the carrier gas. Under trapping conditions, which are created within the analyzer region 40 by adjusting at least one of the above-mentioned parameters to a different value, the selectively transmitted ions accumulate within a 3-dimensional region of space proximate the curved surface terminus 33. Under near-trapping conditions the ions also accumulate within the 3-dimensional region of space proximate the curved surface terminus 33, except that a lower ion density is achieved when operating under near-trapping conditions, since the ions are being continually extracted from the 3-dimensional region of space as an approximately collimated beam of ions. The extracted ions are carried by the carrier gas flow through the ion outlet orifice 42.

Referring still to FIG. 2a, an infrared light source 50 is provided for launching infrared light, shown schematically with a dashed line ending with an open-headed arrow, through a first optical port 48 in the outer FAIMS electrode 44. For example, the infrared light source 50 produces infrared light and directs a beam of the produced infrared light along an optical path including the first optical port 48. Preferably, the first optical port 48 is disposed along the length of the outer electrode 44 at a point that is substantially aligned with the 3-dimensional region of space proximate the spherical terminus 33. Accordingly, the infrared light from infrared light source 50 is directed through a region of higher ion density of the selectively transmitted ions within the 3-dimensional region of space. A second optical port 49 is disposed within the outer FAIMS electrode 44 at a point that is approximately opposite the first optical port 48, for receiving the infrared light after it has passed through the 3-dimensional region of space proximate the spherical terminus 33. A light detector 52 is provided in optical communication with the second optical port 49 for receiving infrared light propagating therethrough, and for providing an electrical signal relating to an intensity of the received infrared light. Of course, the first optical port 48 and the second optical port 49 are preferably of a size that is sufficiently large to support the propagation of the infrared light therethrough. Furthermore, the first optical port 48 and the second optical port 49 are preferably of a size that is sufficiently small such that the electric fields within the analyzer region are substantially unaffected by the discontinuity in the electrode material.

During use, trapping conditions are preferably maintained within the analyzer region as described above, such that the selectively transmitted ions accumulate within the 3-dimensional region of space adjacent to the spherical terminus 33 of the inner electrode 32. This region of space becomes enriched with ions relative to other regions of space within the analyzer region. The infrared light beam is passed through the 3-dimensional region of space, where the accumulated ions may absorb some of the infrared light. The absorption of infrared light is detected at the light detector 52. Preferably, the absorption is measured as a function of frequency of the infrared light. By scanning the frequency of the infrared light, a fingerprint spectrum is obtained that is specific for a given compound. A common method for determining the identity of an unknown compound using solid samples involves comparing the unknown sample with a library of known compounds and reporting the most likely matches. A similar library can be envisioned using gas-phase ions. In this way, the infrared light beam is used to probe ions within the FAIMS analyzer region 40. Accordingly, the infrared light source 50 is an example of a probe signal generator. Of course, light having a wavelength selected from other regions of the electromagnetic spectrum may also be used to probe the ions, such as for example ultraviolet light and visible light. Furthermore, in addition to simply measuring the amount of light that is absorbed by the ions, probing of the ions may include any interaction between an incident light beam and the ions that results in a change to either the ions or the light beam. For example, probing may result in a conformational change to the ions, a dissociation of neutral or charged species from cluster ions, a change of the vibrational state of the ions etc. Further still, probing may result in one of absorption of a portion of the incident light beam, scattering of a portion of the incident light beam, fluorescence by the ions, and emission of light by one of the ions and the gas molecules in the vicinity of the ions.

Optionally, the analyzer is operated in the near-trapping mode so as to continually extract ions from the 3-dimensional region of space. For example, the extracted ions are provided to one of a second FAIMS device and a mass spectrometer for additional separation and detection. Further optionally, the analyzer is operated in a pulsed trapping mode so as to provide packets of ions at intervals of time for one of additional separation and detection.

Figure 2B:
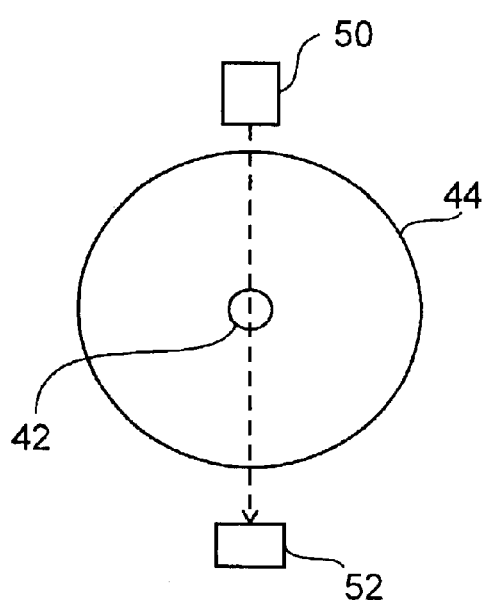

Referring now to FIG. 2b, shown is a simplified end-on view of the FAIMS device of FIG. 2a. Elements labeled with the same numerals have the same function as those illustrated in FIG. 2a. In particular, the infrared light source 50 and the light detector 52 are arranged one relative to the other and relative to the FAIMS outer electrode 44 such that the infrared light travels between the source 50 and the detector 52 through the 3-dimensional region of space proximate the spherical terminus 33. As such, the infrared radiation is used to probe an area of higher ion density within the FAIMS analyzer region 40. It is an advantage of the apparatus according to the first embodiment of the instant invention that the infrared light that is used to probe the accumulated ions does not result in the ions being consumed or structurally changed. Accordingly, ions that are detected can be subsequently analyzed or otherwise manipulated using complimentary analysis methods or complimentary separation techniques, respectively. Furthermore, the ability to increase the concentration of ions in the gas phase, thereby overcoming the natural tendency of the like-charged ions to repel one-another, makes it possible to perform optical detection of samples that otherwise would be far too dilute to provide meaningful results.

Figure 2C:
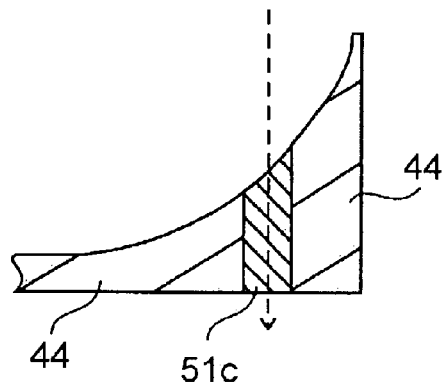

Referring now to FIG. 2c, shown is an enlarged simplified view of a first optical port configuration for use with the FAIMS device according to the first embodiment of the instant invention. A light transmissive window 51c is disposed within the outer electrode 44. The light transmissive window 51c is constructed of a material, other than a gas, that is substantially transmissive to light within a wavelength range of interest. For example, the light transmissive window 51c is constructed of a material that is substantially transmissive to light within the infrared region of the electromagnetic spectrum. Suitable materials for constructing the light transmissive window 51c will be readily apparent to one of skill in the art. Some non-limiting examples of suitable window materials include; sodium chloride (NaCl), potassium bromide (KBr) and calcium chloride (CaCl$_2$). Preferably, the first optical port 48 and the second optical port 49 each include a light transmissive window 51c that is constructed using similar materials. Preferably, the light transmissive window 51c forms a gas tight seal with the outer electrode 44. Preferably, the light transmissive window 51c includes a first outer surface that is approximately continuous with an inner surface of the outer electrode 44, and a second outer surface that is approximately continuous with an outer surface of the outer electrode 44.

Figure 2D:
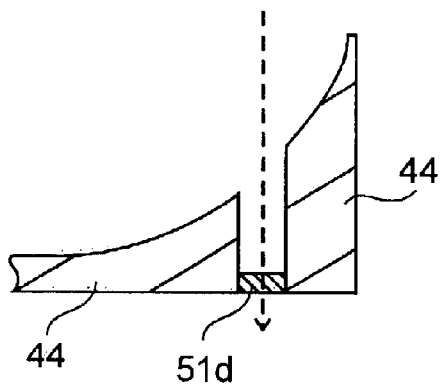

Referring now to FIG. 2d, shown is an enlarged simplified view of a second optical port configuration for use with the FAIMS device according to the first embodiment of the instant invention. A light transmissive window 51d is disposed within the outer electrode 44. The light transmissive window 51d is constructed of a material, other than a gas, that is substantially transmissive to light within a wavelength range of interest. For example, the light transmissive window 51d is constructed of a material that is substantially transmissive to light within the infrared region of the electromagnetic spectrum. Preferably, the first optical port 48 and the second optical port 49 each include a light transmissive window 51d that is constructed using similar materials. Preferably, the light transmissive window 51d forms a gas tight seal with the outer electrode 44. Preferably, the light transmissive window 51d includes a first outer surface recessed within an opening through the outer electrode 44. Since the light transmissive window 51d is generally constructed from an insulating material, ions colliding therewith cause a charge buildup that affects the electric field within the analyzer region due to the applied DV and the applied CV. The effect of such a charge buildup is expected to diminish when the window material is recessed relative to the inner surface of the outer electrode 44.

Figure 2E:
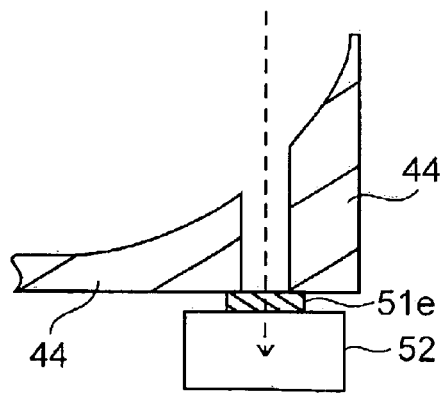

Referring now to FIG. 2e, shown is an enlarged simplified view of a third optical port configuration for use with the FAIMS device according to the first embodiment of the instant invention. An optically transmissive portion 51e of, for example, the light detector 52 is disposed immediately adjacent to the outer surface of the outer electrode 44. Preferably, the optically transmissive portion 51e forms a gas-tight seal against the outer surface of the outer electrode 44. Optionally, the optically transmissive portion 51e is a light transmissive window separate from the light detector 52, which light transmissive window preferably forms a gas-tight seal against the outer surface of the outer electrode 44.

Figure 2F:
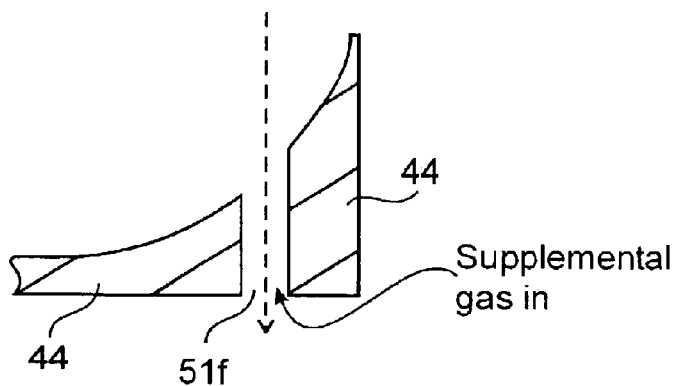

Referring now to FIG. 2f, shown is an enlarged simplified view of a fourth optical port configuration for use with the FAIMS device according to the first embodiment of the instant invention. The fourth optical port configuration does not include a non-gaseous material disposed within an opening through the outer electrode 44. For example, the fourth optical port configuration includes an opening through the outer electrode 44 which allows light to propagate therethrough and which also allows gas and/or ions to escape from the analyzer region 40. Optionally, the fourth optical port configuration includes a source of a supplemental gas flow, as is shown in FIG. 2f, for directing a supplemental gas flow into the analyzer region via the opening through the outer electrode 44, in order to prevent the gas and/or ions from escaping from the analyzer region 40.

Figure 3A:
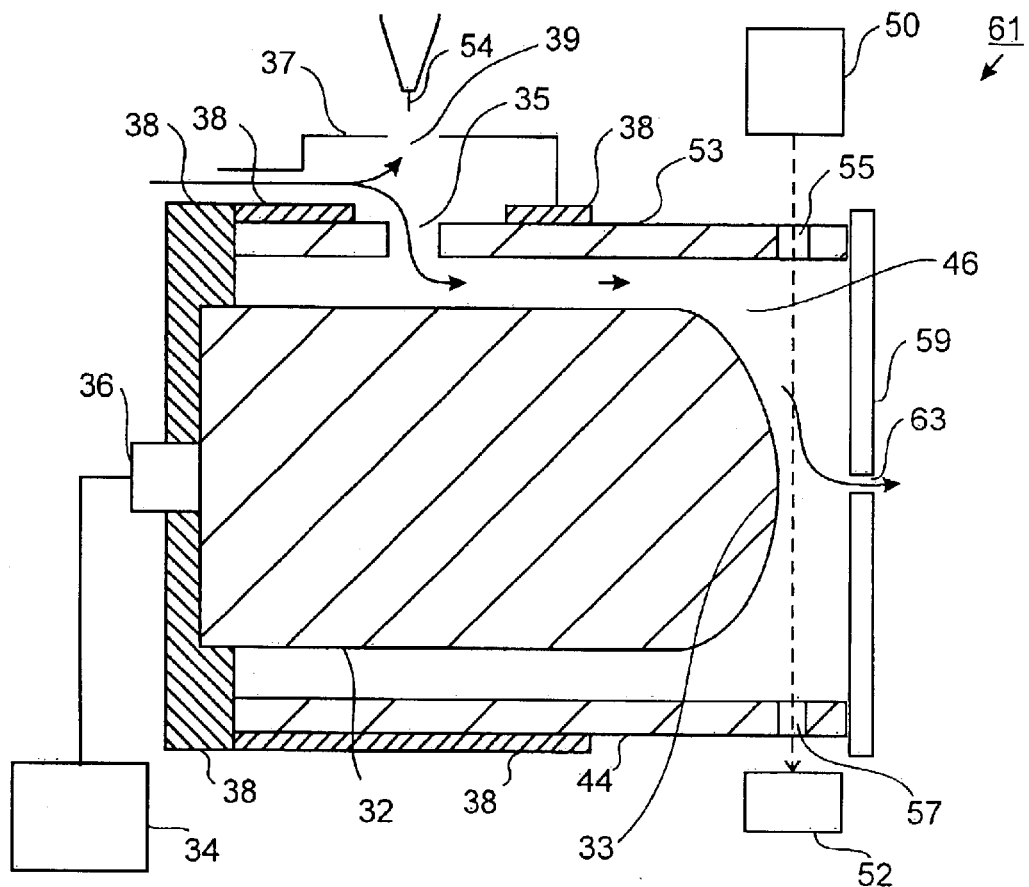
FIG. 3a is a side cross-sectional view of another FAIMS device according to the first embodiment of the instant invention.

Referring now to FIG. 3a, shown is a side cross-sectional view of another FAIMS device 61 according to a first embodiment of the instant invention. Elements labeled with the same numerals have the same function as those illustrated in FIG. 2a. The FAIMS device 61 includes an outer electrode 53 in the form of a tube having an approximately uniform cross-section taken at any point along a longitudinal axis thereof. First and second optical ports 55 and 57, respectively, are provided in the outer electrode 53 for supporting the propagation of light therethrough. The outer electrode 53 does not maintain an approximately constant spacing to the inner electrode 32 about the curved surface terminus 33. Accordingly, an electrically isolated plate, referred to as the trapping plate 59, is disposed adjacent to the outer electrode 53. The trapping plate 59 is used to manipulate the fields in the trapping region adjacent to the spherical terminus 33 of the inner electrode 32. An ion outlet orifice 63 in the trapping plate 59 is provided for extracting ions from the analyzer region 46. The ion outlet orifice 63 in the trapping plate 59 performs substantially the same function as the ion outlet orifice 42 in the outer FAIMS electrode 44 of FIG. 2a. Near-trapping conditions are created within a 3-dimensional region of space within the FAIMS analyzer region 46 and adjacent to the curved surface terminus 33, by adjusting at least one of the carrier gas flow rate, the carrier gas composition, the applied CV, the applied DV, the distance between the curved surface terminus 33 and the ion outlet orifice 63, the temperature of the carrier gas, the pressure of the carrier gas and the potential that is applied to the trapping plate 59.

Figure 3B:
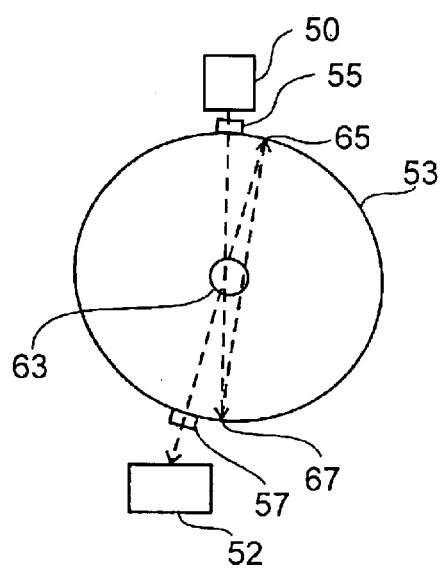

Referring now to FIG. 3b, shown is a simplified end-on view of the FAIMS device of FIG. 3a. Elements labeled with the same numerals have the same function as those illustrated in FIG. 3a. In particular, the infrared source 50 and the detector 52 are arranged relative to each other and relative to the outer electrode 53 such that infrared light from the source 50 travels through the first optical port 55, passes through the 3-dimensional region of space proximate the curved surface terminus 33, and to a first mirror surface 67. The light is redirected by the first mirror surface 67, to pass through the 3-dimensional region of space proximate the curved surface terminus 33 a second time, and to arrive at a second mirror surface 65. Similarly, the second mirror surface redirects the light a second time, to pass through the 3-dimensional region of space proximate the curved surface terminus 33 a third time, after which the light propagates through the second optical port 57, finally arriving at the light detector 52. For example, the first and second mirror surfaces 67 and 65, respectively, are formed by depositing a layer of gold atoms onto the inner surface of the outer electrode 53. Optionally, the first mirror surface 67 directs the infrared light to the second optical port 57 for detection at detector 52. Advantageously, using at least a mirror to redirect the infrared beam increases the effective path length of the infrared light through the sample, thereby providing improved signal to noise when used with dilute samples. Optionally, the infrared source 50 and the detector 52 are arranged relative to each other and relative to the outer electrode 53 such that infrared light from the source 50 travels through the first optical port 55, passes through the 3-dimensional region of space proximate the curved surface terminus 33, propagates through the second optical port 57, and is detected at detector 52.

Figure 4:
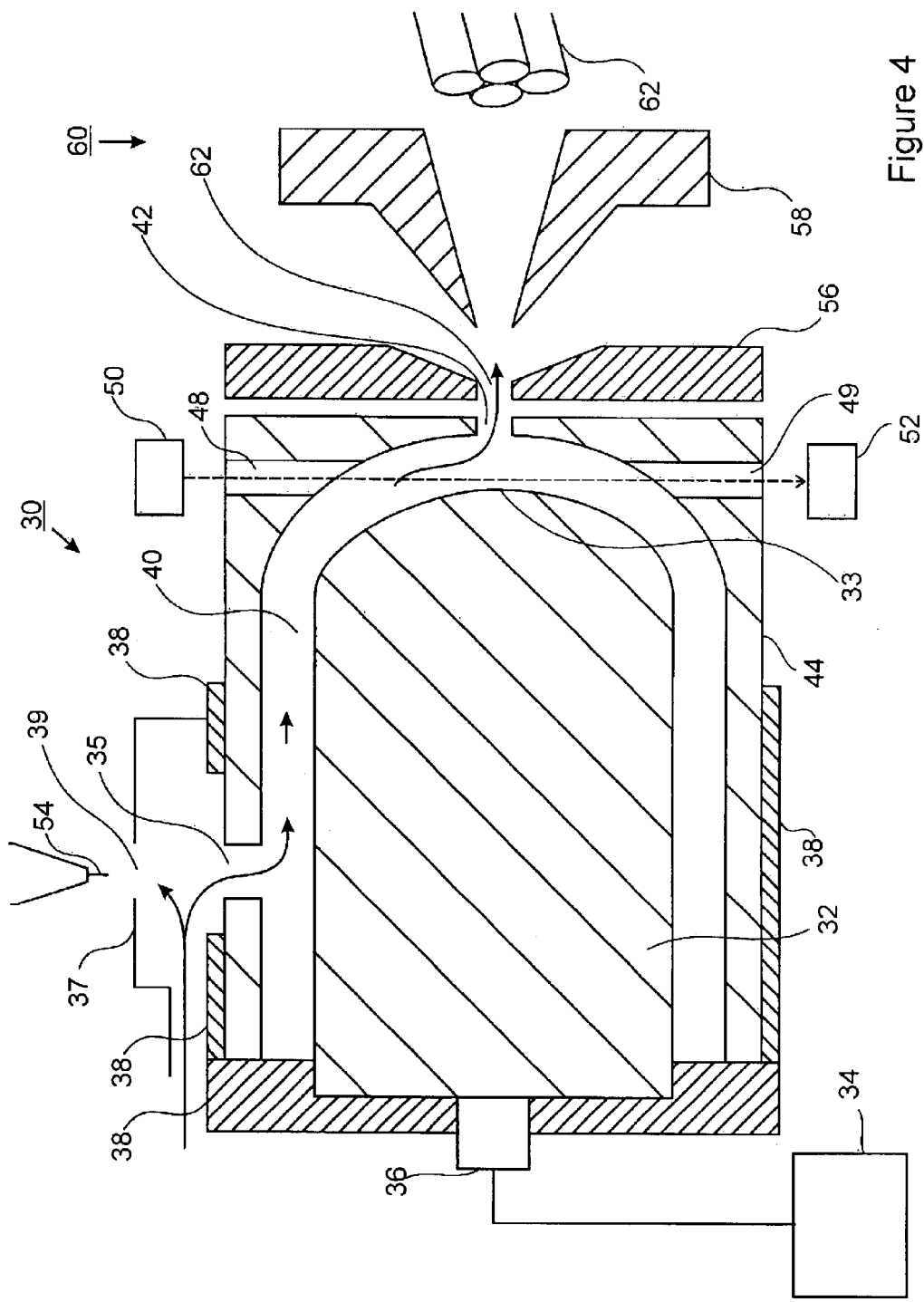
FIG. 4 is a side cross-sectional view of the FAIMS device according to the first embodiment of the instant invention coupled to a mass spectrometer.

Referring now to FIG. 4, shown is a side cross-sectional view of the FAIMS device according to the first embodiment of the instant invention in a tandem arrangement with a mass spectrometer 60. Elements labeled with the same numerals have the same function as those illustrated in FIG. 2a. The ability to confine ions near the spherical terminus 33 of the inner FAIMS electrode 32 supports the use of complementary methods of detection. Ions that are selectively transmitted and trapped by the applied DV and CV can be probed using infrared light, as described with reference to FIG. 2a. Since the infrared analysis does not consume the ions, these same ions can be extracted into a mass spectrometer 60 for further analysis. In particular, an orifice plate 56 of the mass spectrometer 60 is positioned adjacent to the ion outlet orifice 42 in the outer FAIMS electrode 44. Ions that exit from the FAIMS analyzer region 40 through the ion outlet orifice 42 enter the mass spectrometer 60 after passing through an orifice 62 in the orifice plate 56, travel to a skimmer cone 58 within the differentially pumped region of the mass spectrometer, and are mass analyzed within a mass analyzer 62.

In principle, the infrared radiation can also be used to modify the ions while they are trapped in the 3-dimensional region of space proximate the spherical terminus 33 of the inner FAIMS electrode 32. For example, the infrared radiation can be used to change the conformation of protein ions or to dissociate loosely held clusters or complexes. Provided that the newly formed "daughter" ions have a stable trajectory under the ambient CV and DV conditions, it is then possible to detect the daughter ions using one of optical and mass spectrometric methods.

Figure 5:
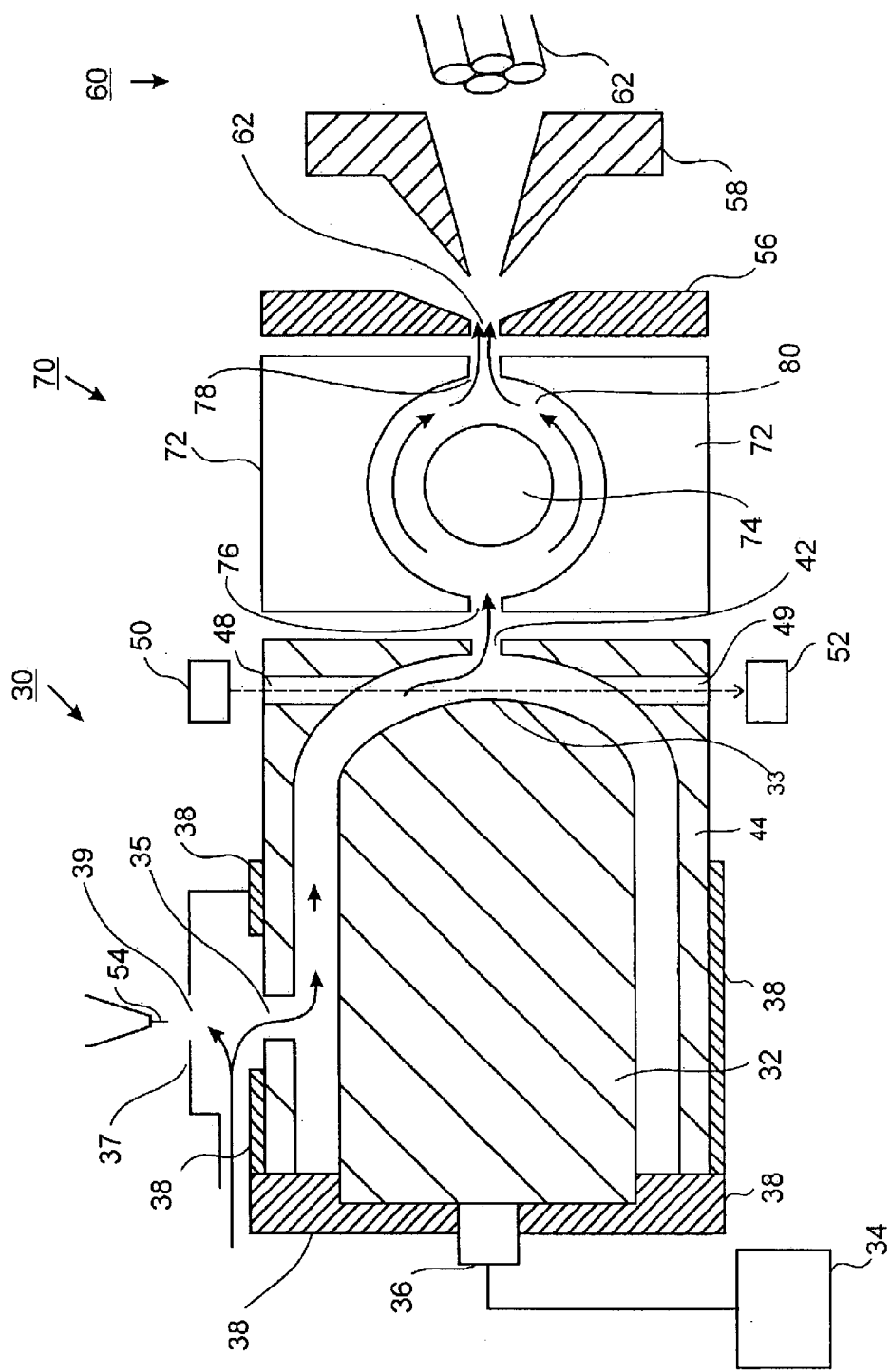
FIG. 5 is a side cross-sectional view of the FAIMS device according to the first embodiment of the instant invention coupled to a second FAIMS device and a mass spectrometer.

Referring now to FIG. 5, shown is a side cross-sectional view of the FAIMS device 30 according to the first embodiment of the instant invention coupled to a second FAIMS device 70 and to a mass spectrometer 60. Elements labeled with the same numerals have the same function as those illustrated in FIG. 2a. Ions confined within the 3-dimensional region of space proximate the spherical terminus 33 of the inner FAIMS electrode 32 are probed using infrared radiation launched from source 50 through the first optical port 48 and received at detector 52 after passing through second optical port 49. For example, the infrared light source 50 produces infrared light and directs a beam of the produced infrared light along an optical path including the first optical port 48. The confined ions are then extracted through the orifice 42 and into the second FAIMS 70 through inlet 76. The second FAIMS 70 is a side-to-side FAIMS device, however any other FAIMS electrode geometry could be used to advantage. The ions are selectively transported through a second analyzer region 80 between an inner FAIMS electrode 74 and an outer FAIMS electrode 72. A high voltage asymmetric waveform and a low voltage dc compensation voltage are applied by a second power supply (not shown), to the inner FAIMS electrode 74. Those ions that have stable trajectories under the ambient conditions of CV and DV within the second FAIMS are passed through the outlet orifice 78 to the mass spectrometer 60. Advantageously, a second different separation of the ions can be achieved in order to eliminate some ions that were co-transported through the first FAIMS 30. The second different separation is controlled by varying at least one of the applied DV, the applied CV, the carrier gas rate, the carrier gas composition, etc. Further advantageously, the identity of the ions that are transmitted by the first FAIMS 30 can be confirmed using infrared techniques before the ions are transported into the second FAIMS 70. This allows a user to tune the first FAIMS 30 or the second FAIMS 70 to achieve a desired result.

Figure 6A:
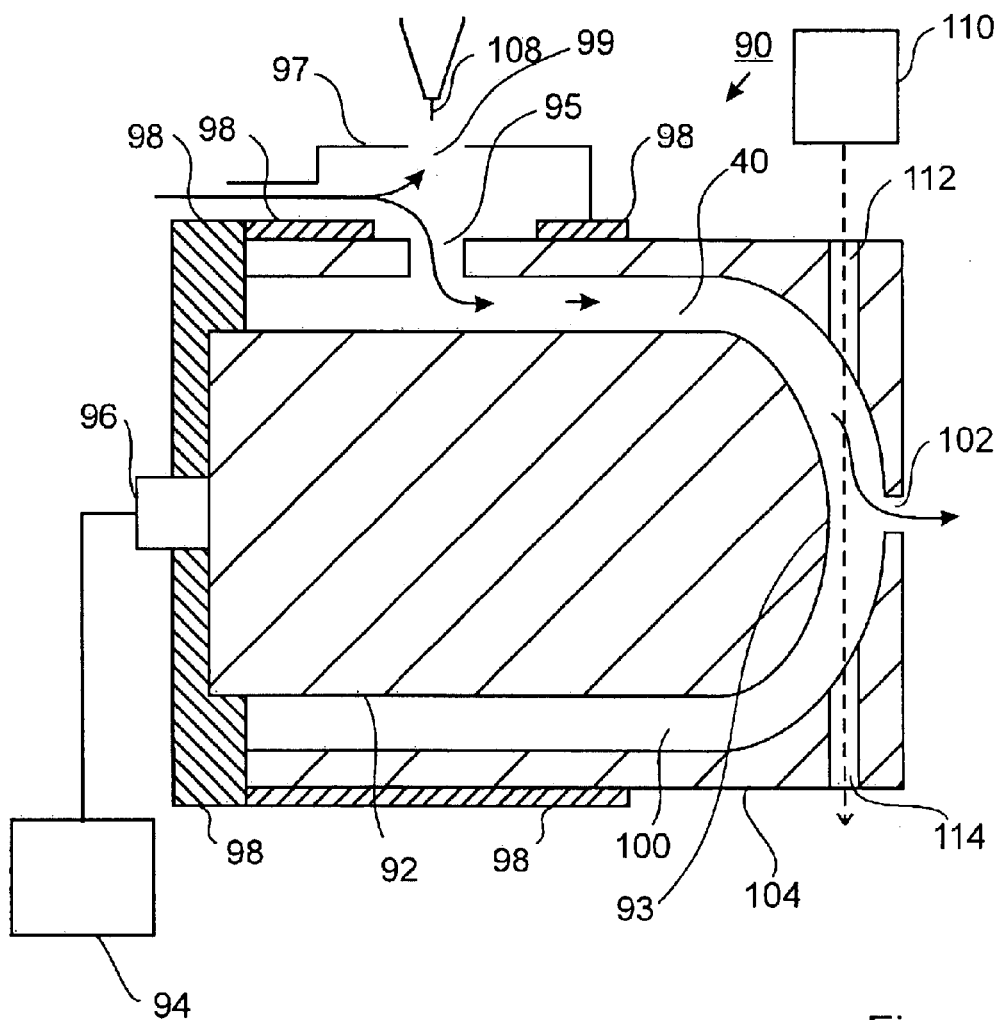
FIG. 6a is a side cross-sectional view of a FAIMS device according to a second embodiment of the instant invention.

Referring now to FIG. 6a, shown is a side cross-sectional view of a FAIMS device 90 according to a second embodiment of the instant invention. The FAIMS device 90, in the form of a domed-FAIMS device, includes inner and outer cylindrical electrodes 92 and 104, respectively, which are supported by an electrically insulating material 98 in an overlapping, spaced-apart arrangement. The generally annular space between the inner electrode 92 and the outer electrode 104 defines a FAIMS analyzer region 100. The width of the analyzer region 100 is approximately uniform around the circumference of the inner electrode 92, and extends around a curved surface terminus 93 of the inner electrode 92. An ion inlet orifice 95 is provided through the outer electrode 104 for introducing ions from an ion source 108 into the analyzer region 100. A flow of a carrier gas, which is represented in the figure by a series of closed-headed arrows, is provided within the analyzer region 100 to carry the ions toward an ion outlet orifice 102 located opposite the curved surface terminus 93 of the inner electrode 92. An orifice 99 within a curtain plate electrode 97 allows for the flow of a portion of the carrier gas in a direction that is counter-current to the direction in which the ions are traveling near the ion inlet 95, so as to desolvate the ions before they are introduced into the analyzer region 100. The inner electrode 92 is provided with an electrical contact 96 through the insulating material 98 for connection to a power supply 94 that during use is capable of applying a high voltage asymmetric waveform voltage (DV) and a low voltage dc compensation voltage (CV) to the inner FAIMS electrode 92.

During use, ions are produced at the ion source 108 from a suitable sample containing a species of interest. Typically, a mixture including a plurality of different ion types is produced when the sample is ionized. A potential gradient is used in order to accelerate the ions of the mixture away from the ion source 108, through the orifice 99 in the curtain plate electrode 97, and toward the ion inlet orifice 95, where the ions become entrained in the carrier gas flow and are carried into the FAIMS analyzer region 100. Once inside the FAIMS analyzer region 100, the ions are carried through an electric field that is formed within the FAIMS analyzer region 100 by the application of the DV and the CV to the inner FAIMS electrode 92 via the electrical contact 96. Ion separation occurs within the FAIMS analyzer region 100 on the basis of the high field mobility properties of the ions. Those ions of the mixture that have a stable trajectory for a particular combination of DV and CV are selectively transmitted through the FAIMS analyzer region 100, whilst other ions of the mixture collide with an electrode surface and are lost. Since the electric field also extends around the curved surface terminus 93, the selectively transmitted ions tend to be directed generally radially inwardly towards the ion outlet orifice 102. Near trapping conditions are created within the analyzer region 100 by adjusting at least one of the carrier gas flow rate, the carrier gas composition, the applied CV, the applied DV, the distance between the curved surface terminus 93 and the ion outlet orifice 102, the temperature of the carrier gas and the pressure of the carrier gas. Under trapping conditions, which are created within the analyzer region 100 by adjusting at least one of the above-mentioned parameters to a different value, the selectively transmitted ions accumulate within a 3-dimensional region of space proximate the curved surface terminus 93. Under near-trapping conditions the ions also accumulate within the 3-dimensional region of space proximate the curved surface terminus 93, except that a lower ion density is achieved when operating under near-trapping conditions, since the ions are being continually extracted from the 3-dimensional region of space as an approximately collimated beam of ions. The extracted ions are carried by the carrier gas flow through the ion outlet orifice 102.

According to the second embodiment of the instant invention, the detection of ions confined in the trapping region of a FAIMS device is performed using a light scattering technique. Raman spectroscopy is a non-limiting example of a light scattering technique suitable for use with the second embodiment of the instant invention. If, during a collision between a photon and an ion in the gas phase, the energy of the photon corresponds to an energy difference between the state that the ion is in and a higher state, the photon may be absorbed. However, no matter what the energy of the photon is, the photon-ion collision may scatter the photon, thereby changing the photon's direction of motion. Most of the scattered photons undergo no change in frequency and energy. A small fraction however, exchange energy with the ion during the collision process. The resulting increase or decrease in energy of the scattered photons is the Raman effect.

Referring still to FIG. 6a, a light source 110 is provided for launching substantially monochromatic light, shown schematically with a dashed line ending with an open-headed arrow, through a first optical port 112 in the outer FAIMS electrode 104. For example, the light source 110 produces substantially monochromatic light and directs a beam of the produced substantially monochromatic along an optical path including the first optical port 112. Preferably, the light source 110 is in the form of a laser light source for providing laser light of any convenient frequency $v_o$, where $v_o$ usually lies in the visible or near-UV region. Preferably, the first optical port 112 is disposed along the length of the outer electrode 104 at a point that is substantially aligned with the 3-dimensional region of space proximate the spherical terminus 93. Accordingly, the light from light source 110 is directed through a region of higher ion density within the 3-dimensional region of space. A second optical port 114 is disposed within the outer FAIMS electrode 104 at a point that is approximately opposite the first optical port 112. Light that is not scattered by ions within the 3-dimensional region of space proximate the spherical terminus 93 is transmitted out of the FAIMS device 90 through the second optical port 114. Optionally, a beam stop is provided in optical communication with the second optical port 114.

Figure 6B:
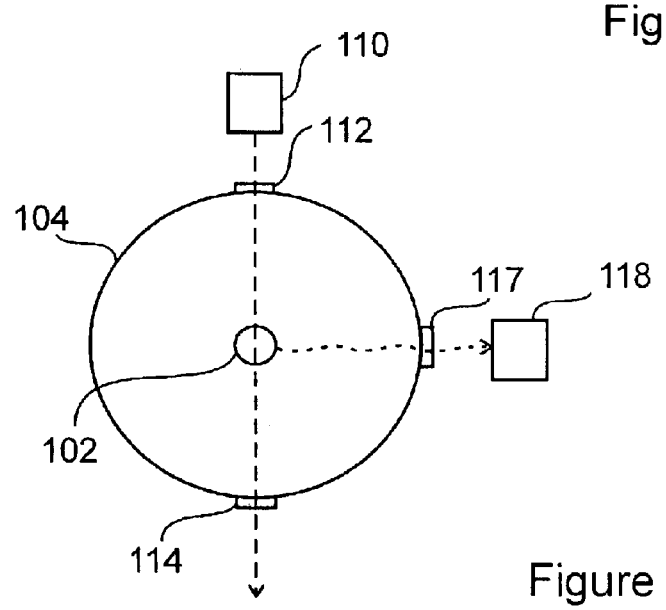

Referring now to FIG. 6b, shown is a simplified end-on view of the FAIMS device of FIG. 6a. Elements labeled with the same numerals have the same function as those illustrated in FIG. 6a. A detector 118 is provided in optical communication with a third optical port 117 for receiving the light, shown as a wavy dotted line, that is scattered from the ions confined within the 3-dimensional region of space proximate the curved terminus 93 of the inner FAIMS electrode 92. The third optical port 117 is constructed to be substantially transmissive to the scattered light. Preferably, the third optical port 117 is disposed such that the incident laser light is substantially precluded from impinging upon the detector 118 whilst the scattered light is being observed. The detector 118 provides an electrical signal relating to an intensity of the scattered light. Of course, the first optical port 112 and the third optical port 117 are preferably of a size that is sufficiently large to support the propagation of the incident laser light and the scattered light, respectively, therethrough. Furthermore, the first optical port 112, the second optical port 114 and the third optical port 117 are preferably of a size that is sufficiently small such that the electric fields within the analyzer region are substantially unaffected by the discontinuity in the electrode material. Optionally, one of the optical port configurations described with reference to FIGS. 2c to 2f may be used with the FAIMS device 90 according to the second embodiment of instant invention.

During use, trapping conditions are maintained within the analyzer region 100 as described above, such that the selectively transmitted ions accumulate within the 3-dimensional region of space adjacent to the spherical terminus 93 of the inner electrode 92. This region of space becomes enriched with ions relative to other regions of space within the analyzer region. The incident laser light is passed through the 3-dimensional region of space, where the accumulated ions may scatter some of the laser light. Of course, the scattering cross section of ions is very small, hence a sufficiently high ion density and an intense laser beam are necessary in order to achieve an amount of scattering that can be detected at detector 118.

Optionally, the analyzer is operated in the near-trapping mode so as to continually extract ions from the 3-dimensional region of space. For example, the extracted ions are provided to one of a second FAIMS device and a mass spectrometer for additional separation and detection. Further optionally, the analyzer is operated in a pulsed trapping mode so as to provide packets of ions at intervals of time for one of additional separation and detection.

Figure 7A:
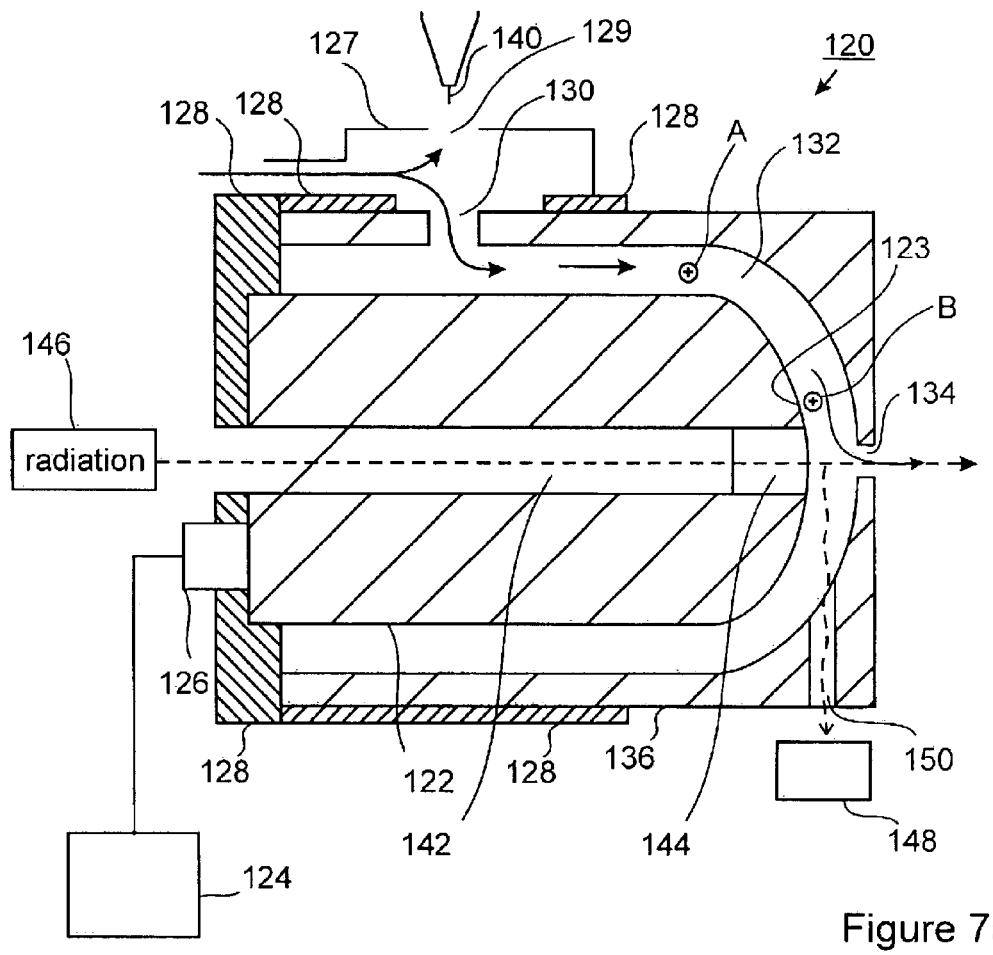
FIG. 7a is a side cross-sectional view of another FAIMS device according to the second embodiment of the instant invention.

Referring now to FIG. 7a, shown is a side cross-sectional view of another FAIMS device 120 according to the second embodiment of the instant invention. The FAIMS device 120, in the form of a domed-FAIMS device, includes inner and outer cylindrical electrodes 122 and 136, respectively, which are supported by an electrically insulating material 128 in an overlapping, spaced-apart arrangement. The generally annular space between the inner electrode 122 and the outer electrode 136 defines a FAIMS analyzer region 132. The width of the analyzer region 132 is approximately uniform around the circumference of the inner electrode 122, and extends around a curved surface terminus 123 of the inner electrode 122. An ion inlet orifice 130 is provided through the outer electrode 136 for introducing ions from an ion source 140 into the analyzer region 132. A flow of a carrier gas, which is represented in the figure by a series of closed-headed arrows, is provided within the analyzer region 132 to carry the ions toward an ion outlet orifice 134 located opposite the curved surface terminus 123 of the inner electrode 122. An orifice 129 within a curtain plate electrode 127 allows for the flow of a portion of the carrier gas in a direction that is counter-current to the direction in which the ions are traveling near the ion inlet 130, so as to desolvate the ions before they are introduced into the analyzer region 132. The inner electrode 122 is provided with an electrical contact 126 through the insulating material 128 for connection to a power supply 124 that during use is capable of applying a high voltage asymmetric waveform voltage (DV) and a low voltage dc compensation voltage (CV) to the inner FAIMS electrode 122.

During use, ions are produced at the ion source 140 from a suitable sample containing a species of interest. Typically, a mixture including a plurality of different ion types is produced when the sample is ionized. A potential gradient is used in order to accelerate the ions of the mixture away from the ion source 140, through the orifice 129 in the curtain plate electrode 127, and toward the ion inlet orifice 130, where the ions become entrained in the carrier gas flow and are carried into the FAIMS analyzer region 132. Once inside the FAIMS analyzer region 132, the ions are carried through an electric field that is formed within the FAIMS analyzer region 132 by the application of the DV and the CV to the inner FAIMS electrode 122 via the electrical contact 126. Ion separation occurs within the FAIMS analyzer region 132 on the basis of the high field mobility properties of the ions. Those ions of the mixture that have a stable trajectory for a particular combination of DV and CV are selectively transmitted through the FAIMS analyzer region 132, whilst other ions of the mixture collide with an electrode surface and are lost. Since the electric field also extends around the curved surface terminus 123, the selectively transmitted ions tend to be directed generally radially inwardly towards the ion outlet orifice 134. Near trapping conditions are created within the analyzer region 132 by adjusting at least one of the carrier gas flow rate, the carrier gas composition, the applied CV, the applied DV, the distance between the curved surface terminus 123 and the ion outlet orifice 134, the temperature of the carrier gas and the pressure of the carrier gas. Under trapping conditions, which are created within the analyzer region 132 by adjusting at least one of the above-mentioned parameters to a different value, the selectively transmitted ions accumulate within a 3-dimensional region of space proximate the curved surface terminus 123. Under near-trapping conditions the ions also accumulate within the 3-dimensional region of space proximate the curved surface terminus 123, except that a lower ion density is achieved when operating under near-trapping conditions, since the ions are being continually extracted from the 3-dimensional region of space as an approximately collimated beam of ions. The extracted ions are carried by the carrier gas flow through the ion outlet orifice 134.

Referring still to FIG. 7a, the FAIMS inner electrode 122 has a channel 142 extending therethrough. A first optical port 144 is disposed within the channel 142, proximate the curved surface terminus 123. A light source 146 is provided for launching substantially monochromatic light, shown schematically with a dashed line ending with an open arrow, into the channel 142 and through the first optical port 144 in the inner FAIMS electrode 122. For example, the light source 146 produces substantially monochromatic light and directs a beam of the produced substantially monochromatic light along an optical path including the first optical port 144. Preferably, the light source 146 is in the form of a laser light source for providing laser light of any convenient frequency $v_o$, where $v_o$ usually lies in the visible or near-UV region. Ions that are confined in the trapping region scatter a portion of the incident radiation with a portion thereof going to a detector 148 after passing through a second optical port 150 in the outer FAIMS electrode 136. Light that is not scattered by ions within the 3-dimensional region of space proximate the spherical terminus 123 is transmitted out of the FAIMS device 120 through the ion outlet orifice 134. Optionally, a beam stop is provided in optical communication with the ion outlet orifice 134. Of course, the first optical port 144 and the second optical port 150 are preferably of a size that is sufficiently large to support the propagation of the incident laser light and the scattered light, respectively, therethrough. Furthermore, the first optical port 144 and the second optical port 150 are preferably of a size that is sufficiently small such that the electric fields within the analyzer region are substantially unaffected by the discontinuity in the electrode material. Optionally, one of the optical port configurations described with reference to FIGS. 2c to 2f may be used with the FAIMS device 120 according to the second embodiment of instant invention.

Figure 7B:
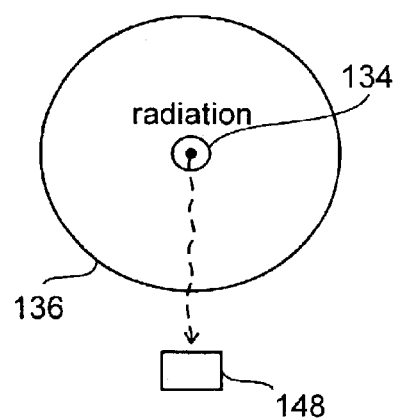

Referring now to FIG. 7b, shown is a simplified end-on view of the FAIMS device of FIG. 7a. Elements labeled with the same numerals have the same function as those illustrated in FIG. 7a. The black dot in FIG. 7b indicates from this view that the laser radiation is coming out of the page toward the reader. In this case, the scattered light is observed at right angles to the incident laser light. Of course, the scattered light may be observed at any appropriate angle. The detector 148 provides an electrical signal relating to an intensity of the scattered light.

In addition to the incident light being scattered by interactions with the ions confined within the FAIMS analyzer, light scattering also occurs if the ions heat a small volume of the surrounding bath gas. The photons of the incident light scatter as they pass into a hot gas because such a heated "bubble" of gas has a different refractive index than the cooler surrounding gas. One way of inducing the ions to heat a small volume of the surrounding bath gas is to adjust the asymmetric waveform that is applied to the inner electrode of a FAIMS device. Since the application of the asymmetric waveform results in the ions oscillating back and forth in approximately a same region of space, the gas that surrounds an ion becomes heated around the trajectory of the ion. This oscillation requires energy, and this energy is dissipated to create a region in the vicinity of the ion where the gas is hotter than the bulk of the gas in the FAIMS device. This region of heated gas is significantly larger in size than the ion, and is more likely to scatter the light than the relatively small ion itself. Of course, the oscillation of any ion present in the trapping region gives rise to heating of the bath gas. In other words, the ions that are detected may not be the ion of interest, despite the fact that they are transmitted at the same CV value. Accordingly, there may not be as much specificity as there would be in looking at the scattered light from the ion itself, as described above. Tandem FAIMS devices may be more appealing for studying gas phase ions based on the heating of the bath gas because of the extra specificity as opposed to a single FAIMS device. Alternatively, the non-destructive nature of the detection method supports the combination of light scattering detection methods with mass spectrometry in order to achieve more specificity if desired.

The FAIMS device 90 that was described with reference to FIGS. 6a and 6b, as well as the FAIMS device 120 that was described with reference to FIGS. 7a and 7b, is suitable for detecting ions based upon the scattering of incident light as a result of bath gas heating by the ions. Application of a high voltage, high frequency asymmetric waveform to the ions in the analyzer region of FAIMS causes the ions to move rapidly back and forth through the gas in an oscillatory motion. The energy provided to the ions to cause this motion is dissipated, effectively by the equivalent of friction, to the gas and causes heating of the gas in the vicinity of the ion. This heated gaseous region becomes a lens of different refractive index than the bulk gas, and can scatter incident light. If the ion is being carried along the analyzer region of FAIMS, the ion and the heated region remain together as they move in concert along the length of the analyzer. The heat produced by the ion therefore continues to heat the same volume of gas, whose temperature continues to rise. On the other hand, if the ion enters a trapping or near trapping region of FAIMS this condition changes. The ion is constrained by the focusing effects of the electric fields, and the gas flows past the ion. In this case the heat generated by the oscillating ion is applied to continuously new volumes of gas that flow past the ion, and the heat is carried away by the flow of gas.

For example, in FIG. 7a, an ion A is flowing along with the gas as described in the first case in the previous paragraph. This maximizes the temperature of the gas in the vicinity of ion A. On the other hand an ion B, which is located within the 3-dimensional region of space proximate the curved surface terminus 123 of the inner electrode 122, feels the contrary forces of the electric fields and gas flows, and some of the heat produced by the ion B is carried away by the gas out of the orifice 134.

Figure 8:
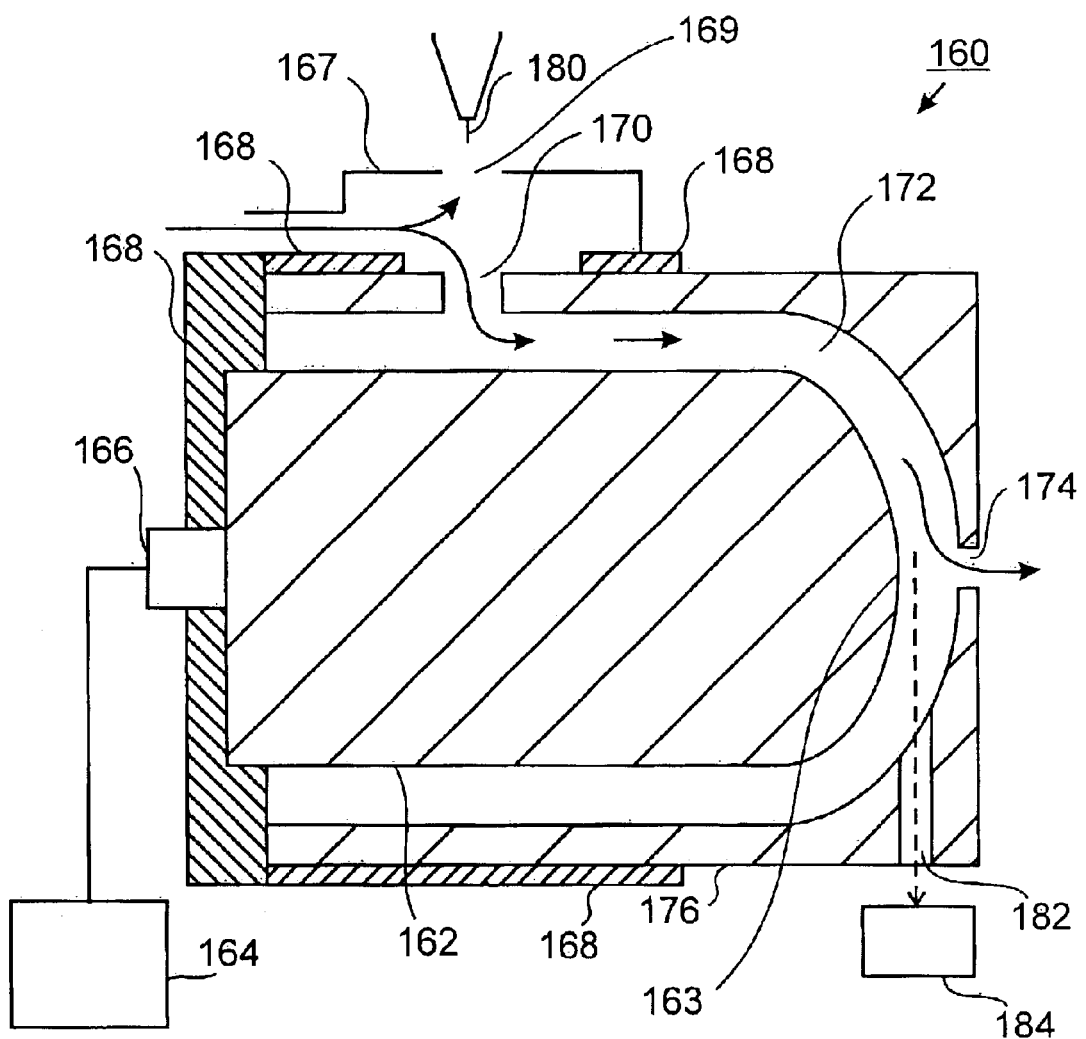
FIG. 8 is a side cross-sectional view of a FAIMS device according to a third embodiment of the instant invention.

Referring now to FIG. 8, shown is a side cross-sectional view of a FAIMS device 160 according to a third embodiment of the instant invention. The FAIMS device 160, in the form of a domed-FAIMS device, includes inner and outer cylindrical electrodes 162 and 176, respectively, which are supported by an electrically insulating material 168 in an overlapping, spaced-apart arrangement. The generally annular space between the inner electrode 162 and the outer electrode 176 defines a FAIMS analyzer region 172. The width of the analyzer region 172 is approximately uniform around the circumference of the inner electrode 162, and extends around a curved surface terminus 163 of the inner electrode 162. An ion inlet orifice 170 is provided through the outer electrode 176 for introducing ions from an ion source 180 into the analyzer region 172. A flow of a carrier gas, which is represented in the figure by a series of closed-headed arrows, is provided within the analyzer region 172 to carry the ions toward an ion outlet orifice 174 located opposite the curved surface terminus 163 of the inner electrode 162. An orifice 169 within a curtain plate electrode 167 allows for the flow of a portion of the carrier gas in a direction that is counter-current to the direction in which the ions are traveling near the ion inlet 170, so as to desolvate the ions before they are introduced into the analyzer region 172. The inner electrode 162 is provided with an electrical contact 166 through the insulating material 168 for connection to a power supply 164 that during use is capable of applying a high voltage asymmetric waveform voltage (DV) and a low voltage dc compensation voltage (CV) to the inner FAIMS electrode 162.

During use, ions are produced at the ion source 180 from a suitable sample containing a species of interest. Typically, a mixture including a plurality of different ion types is produced when the sample is ionized. A potential gradient is used in order to accelerate the ions of the mixture away from the ion source 180, through the orifice 169 in the curtain plate electrode 167, and toward the ion inlet orifice 170, where the ions become entrained in the carrier gas flow and are carried into the FAIMS analyzer region 172. Once inside the FAIMS analyzer region 172, the ions are carried through an electric field that is formed within the FAIMS analyzer region 172 by the application of the DV and the CV to the inner FAIMS electrode 162 via the electrical contact 166. Ion separation occurs within the FAIMS analyzer region 172 on the basis of the high field mobility properties of the ions. Those ions of the mixture that have a stable trajectory for a particular combination of DV and CV are selectively transmitted through the FAIMS analyzer region 172, whilst other ions of the mixture collide with an electrode surface and are lost. Since the electric field also extends around the curved surface terminus 163, the selectively transmitted ions tend to be directed generally radially inwardly towards the ion outlet orifice 174. Near trapping conditions are created within the analyzer region 172 by adjusting at least one of the carrier gas flow rate, the carrier gas composition, the applied CV, the applied DV, the distance between the curved surface terminus 163 and the ion outlet orifice 174, the temperature of the carrier gas and the pressure of the carrier gas. Under trapping conditions, which are created within the analyzer region 172 by adjusting at least one of the above-mentioned parameters to a different value, the selectively transmitted ions accumulate within a 3-dimensional region of space proximate the curved surface terminus 163. Under near-trapping conditions the ions also accumulate within the 3-dimensional region of space proximate the curved surface terminus 163, except that a lower ion density is achieved when operating under near-trapping conditions, since the ions are being continually extracted from the 3-dimensional region of space as an approximately collimated beam of ions. The extracted ions are carried by the carrier gas flow through the ion outlet orifice 174.

The applied high voltage asymmetric waveform causes an ion within the analyzer region 172 to experience a rapid oscillatory motion that leads to energetic collisions with the surrounding bath gas. These collisions result in "heating" of an ion as it moves through the bath gas, as was described in more detail above. Ions that are heated by the high electric fields in the FAIMS device may also emit some of their energy. For example, molecules that absorb infrared radiation are also capable of emitting characteristic infrared wavelengths when heated for example by collisions with the bath gas molecules. This emitted radiation can be monitored to probe the ions confined in the trapping region of the FAIMS device. Accordingly, the power supply 164 is another example of a probe signal generator.

Referring still to FIG. 8, the FAIMS device 160 includes an optical port 182 in the outer FAIMS electrode 176. The optical port 182 supports the propagation of infrared light, including infrared light having a wavelength within a wavelength range of interest, therethrough. Preferably, the optical port 182 is disposed along the length of the outer electrode 176 at a point that is substantially aligned with the 3-dimensional region of space proximate the spherical terminus 163. Accordingly, the infrared light emitted by the ions that are confined within the 3-dimensional region of space passes through the optical port 182 to a light detector 184. The detector 184 is in optical communication with the optical port 182 for receiving the emitted infrared light propagating therethrough, and for providing an electrical signal relating to an intensity of the emitted infrared light having a wavelength within the wavelength range of interest. Of course, the optical port 182 is of a size that is sufficiently large to transmit the emitted infrared light. Furthermore, the optical port 182 is sufficiently small such that the electric fields within the analyzer region 172 are substantially unaffected by the discontinuity in the electrode material. Optionally, one of the optical port configurations described with reference to FIGS. 2c to 2f may be used with the FAIMS device 160 according to the third embodiment of instant invention.

Referring still to FIG. 8, the detector 184 is preferably placed proximate the trapping region. Having the detector 184 in the region near the gas outlet 174 reduces the effect of the emission of ions other than the ions of interest compared with having the detector in the region near the ion inlet 170. In addition, the ion density in the trapping region proximate the spherical terminus 163 of the inner FAIMS electrode 162 can be significantly higher than the ion density in the analyzer region when the operating parameters are selected to optimize ion trapping. The higher ion density results in more radiation being emitted from the trapping region and therefore a more intense signal is acquired. The amount of heating required by the application of the asymmetric waveform to trigger characteristic emission events in an ion may be variable. Consequently, emission spectra may be acquired as a function of the DV to give multiple fingerprint spectra that are specific for a given analyte, as a function of DV, since the emission is specific to the structure of the species. As was described above, a common method for determining the identity of an unknown compound using IR detection involves comparing the unknown sample with a library of known compounds and reporting the most likely matches. For this example, however, the emission spectra may change as a function of the applied waveform voltage. Thus, reference spectra at different applied waveform voltages should be used for comparative purposes.

Optionally, the analyzer is operated in the near-trapping mode so as to continually extract ions from the 3-dimensional region of space. For example, the extracted ions are provided to one of a second FAIMS device and a mass spectrometer for additional separation and detection. Further optionally, the analyzer is operated in a pulsed trapping mode so as to provide packets of ions at intervals of time for one of additional separation and detection.

Figure 9:
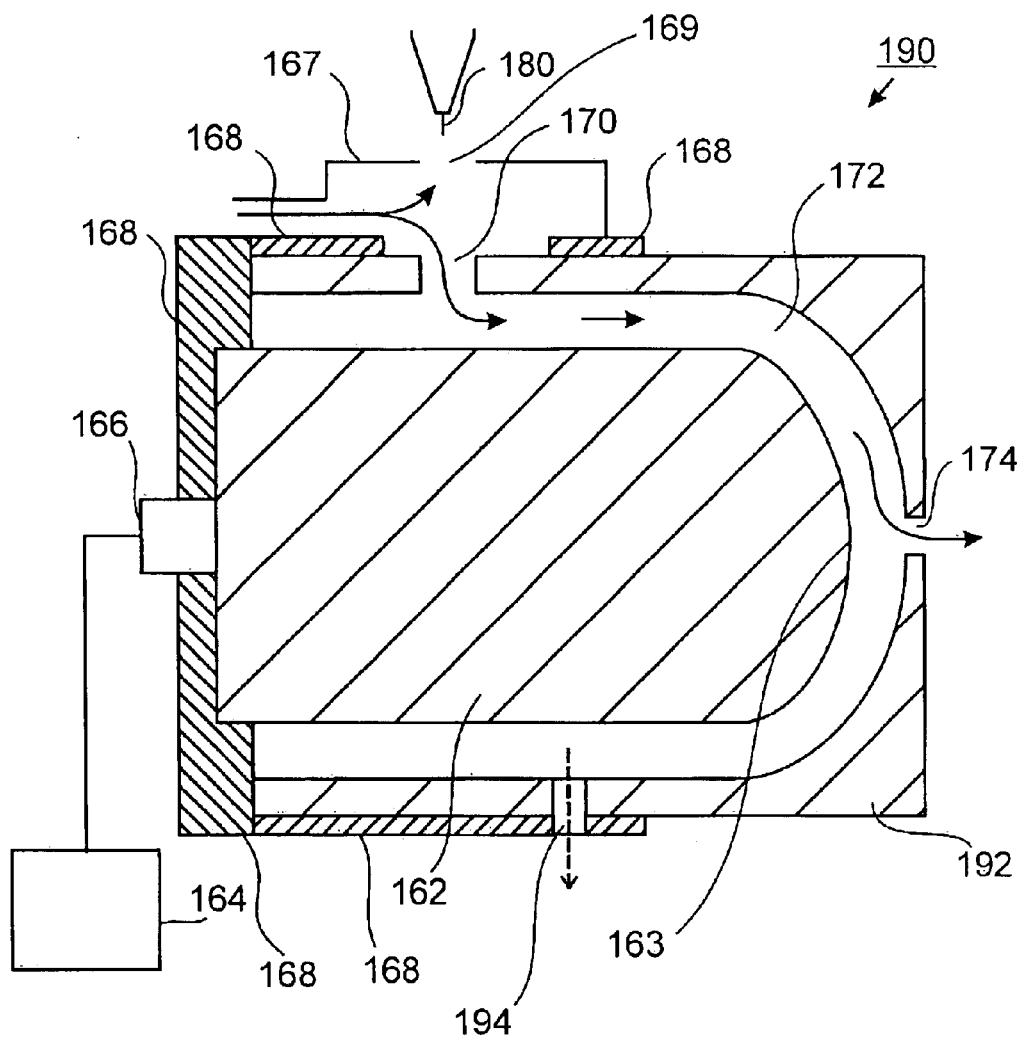
FIG. 9 is a side cross-sectional view of another FAIMS device according to the third embodiment of the instant invention.

Referring now to FIG. 9, shown is a side cross-sectional view of another FAIMS device according to the third embodiment of the instant invention. Elements labeled with the same numerals have the same function as those illustrated in FIG. 8. The FAIMS device 190, in the form of a domed-FAIMS device, includes an outer FAIMS electrode 192 having an optical port 194 that is disposed along a length thereof at a point that is intermediate the ion inlet 170 and the curved surface terminus 163. Of course, heating of the ions occurs throughout the FAIMS device 190 when the asymmetric waveform is operated at high voltage. Thus, the FAIMS device 190 does not require a light source in order to excite the ions within the analyzer region 172, which simplifies the set-up and reduces the cost to produce the apparatus. In addition, the heating of the ions is not restricted to the ions that are confined in the trapping region, but instead ions throughout the FAIMS device experience heating. Thus, the placement of the detector is not as restricted as it is in the first and second embodiments of the instant invention. For the FAIMS device 190, the optical port 194 in the outer FAIMS electrode 192 may be disposed at one of a plurality of locations along the outer FAIMS electrode 192 in the region between the ion inlet and ion outlet. Of course, locating the optical port 194 too close to the ion inlet 170, however, may result in a condition in which there is a greater contribution to the background because of emission from ions other than the ion of interest. This occurs if ions other than the ions of interest have not had sufficient time to be lost to the walls of the FAIMS device 190. That is, ions other than the ion of interest, which transmit at CV values other than the optimal CV value of the ion of interest, require a finite time after they enter the ion inlet before they collide with an electrode wall. This time is dependent upon several parameters that include, but are not limited to, the voltage and frequency of the asymmetric waveform, the CV of the ion in comparison with the ion of interest, etc.

For improved detection specificity, the invention described with reference to FIG. 8 or 9 is optionally combined with mass spectrometry based detection. The nondestructive method of measuring the radiation emitted from the ion of interest enables the ion to be further studied using mass spectrometry based techniques.

Optionally, the FAIMS device shown in FIG. 9 is constructed using other than cylindrical electrode geometry. For instance, a trapping region is not required, and therefore FAIMS devices having, for instance, one of parallel plate electrodes, curved plate electrodes and spherical electrodes are suitable. Furthermore, the so-called side-to-side FAIMS devices could also be used to advantage with the invention as it is described with reference to FIG. 9.

In addition to detecting selectively transmitted ions, the above-mentioned devices are also suitable for affecting a property of the selectively transmitted ions. In principle, the IR light can be used to modify the ions, for example change the conformation of protein ions, or dissociate loosely held clusters or complexes, while the precursors are trapped in the FAIMS device. The newly formed "daughter" ions that are formed from these precursor ions can be detected by optical or mass spectrometric methods. Similarly, bath gas heating resulting from the application of strong electric fields within the FAIMS analyzer region provides the energy that is required to affect the conformation or dissociate clusters within the selectively transmitted ions. Of course, changing the structure of a selectively transmitted ion affects its high field ion mobility properties. As such, a parent ion that has a stable trajectory under a particular combination of applied DV and CV may form a daughter ion that is lost due to a collision with an electrode under identical DV and CV conditions.

Figure 10:
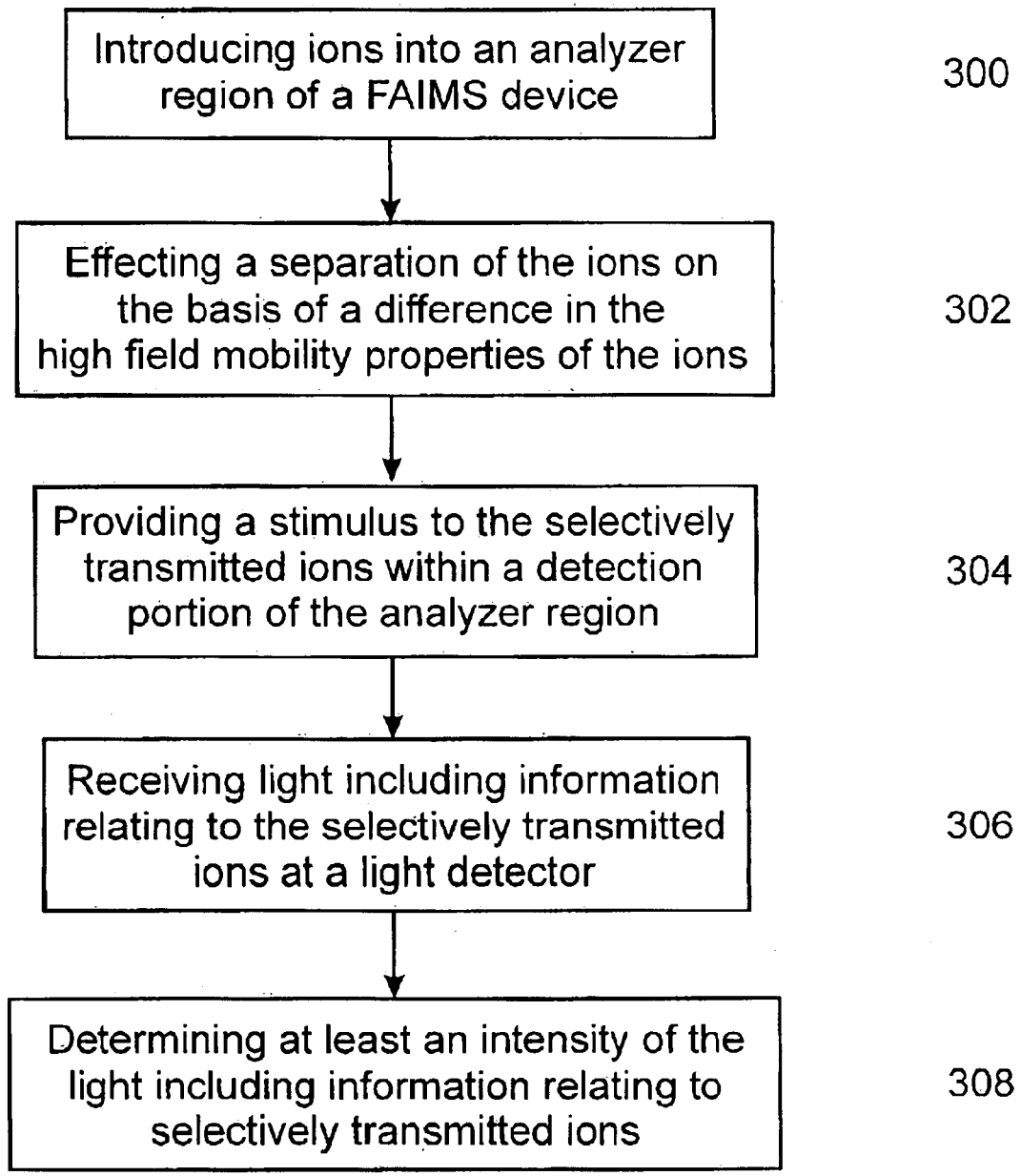
FIG. 10 is a simplified flow diagram for a method of detecting selectively transmitted ions according to the first embodiment of the instant invention.

Referring now to FIG. 10, shown is a simplified flow diagram for a method of detecting selectively transmitted ions using an optical based detection technique. At step 300, a mixture of ions including an ion type of interest is introduced into a FAIMS analyzer region of, for example, one of the above-mentioned FAIMS devices 30, 61, 90, 120, 160 and 190. Optionally, the ions are produced within the analyzer region from a suitable sample using, for example, a laser-based ionization technique. At step 302, appropriate conditions are provided within the FAIMS analyzer region for effecting a separation of the ions, to selectively transmit the ion type of interest to a detection portion of the analyzer region. For optical based detection techniques involving one of an absorption and a scattering of incident radiation by the selectively transmitted ions, it is most preferable to confine the selectively transmitted ions within a 3-dimensional region of space overlapping with the detection portion. Confining the selectively transmitted ions within the 3-dimensional region of space results in a higher ion density within the detection portion of the analyzer region, which produces a better response from the light detector. For optical based detection techniques involving bath gas heating, it is preferable to probe the ions in a portion of the analyzer region other than the 3-dimensional region of space proximate the curved surface terminus of the inner electrode. Once ions are being selectively transmitted through the analyzer region to the detection portion, a stimulus is provided at step 304 to the selectively transmitted ions. For example, providing the stimulus includes one of directing an incident beam of infrared light through the detection portion, directing an incident beam of laser light through the detection portion, and applying a strong electric field within the detection portion. Optionally, a combination including two or more of the above-mentioned stimuli is provided. The stimulus is provided such that light including information relating to the selectively transmitted ions results from an interaction between the stimulus and the selectively transmitted ions. The light including information relating to the selectively transmitted ions depends upon the nature of the stimulus, and includes transmitted infrared light, light that is scattered by one of the selectively transmitted ions and the carrier gas in the vicinity of a selectively transmitted ion, and infrared light emitted by the selectively transmitted ions as a result of bath gas heating of the ions under the influence of strong electric fields within the analyzer region. At step 306 the light including information relating to the selectively transmitted ions is received at a light detector. Preferably, the light is propagated through an optical port to a detector that is disposed external to the FAIMS analyzer region. At step 308, at least an intensity of the light including information relating to the selectively transmitted ions is determined. In this case, the information provides a measure of the ion concentration or of the ion density within the detection portion of the analyzer region. Preferably, the intensity determination is performed as a function of wavelength, in which case the information also relates to a structural identification of the selectively transmitted ions. Optionally, the selectively transmitted ions are provided to a different analyzer or to a mass spectrometer after optical based detection.

Figure 11:
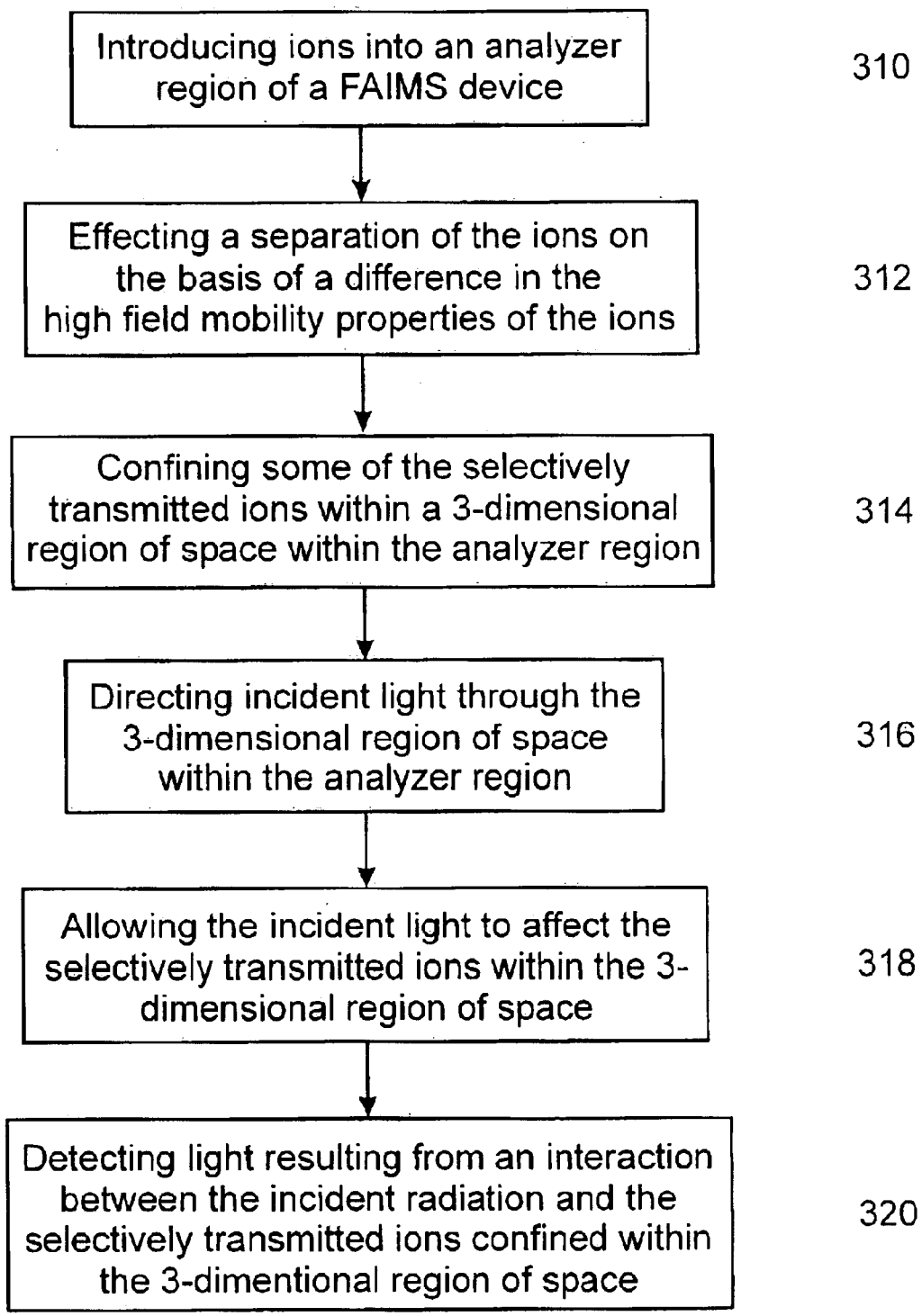
FIG. 11 is a simplified flow diagram for a method of detecting selectively transmitted ions according to the second embodiment of the instant invention.

Referring now to FIG. 11, shown is a simplified flow diagram for another method of detecting selectively transmitted ions using an optical based detection technique. At step 310, a mixture of ions including an ion type of interest is introduced into a FAIMS analyzer region of, for example, one of the above-mentioned FAIMS devices 30, 61, 90 and 120. Optionally, the ions are produced within the analyzer region from a suitable sample using, for example, a laser-based ionization technique. At step 312, appropriate conditions are provided within the FAIMS analyzer region for effecting a separation of the ions, to selectively transmit the ion type of interest to a detection portion of the analyzer region. At step 314, some of the selectively transmitted ions are confined within a 3-dimensional region of space overlapping with the detection portion. Confining the selectively transmitted ions within the 3-dimensional region of space results in a higher ion density within the detection portion of the analyzer region, which produces a better response from the light detector. At step 316, incident light is directed through the 3-dimensional region of space within the analyzer region. For example, light from one of an infrared light source and a laser light source is directed through a first light transmissive optical port in a direction toward the 3-dimensional region of space. At step 318 the incident light is allowed to interact with the selectively transmitted ions confined within the 3-dimensional region of space, to result in light including information relating to the selectively transmitted ions. At step 320, the light including information relating to the selectively transmitted ions is detected. For example, the light propagates from the 3-dimensional region of space to a light detector via a second light transmissive optical port. Optionally, the light is detected after propagating through one of the first light transmissive optical port and the ion outlet orifice from the FAIMS analyzer region.

Figure 12:
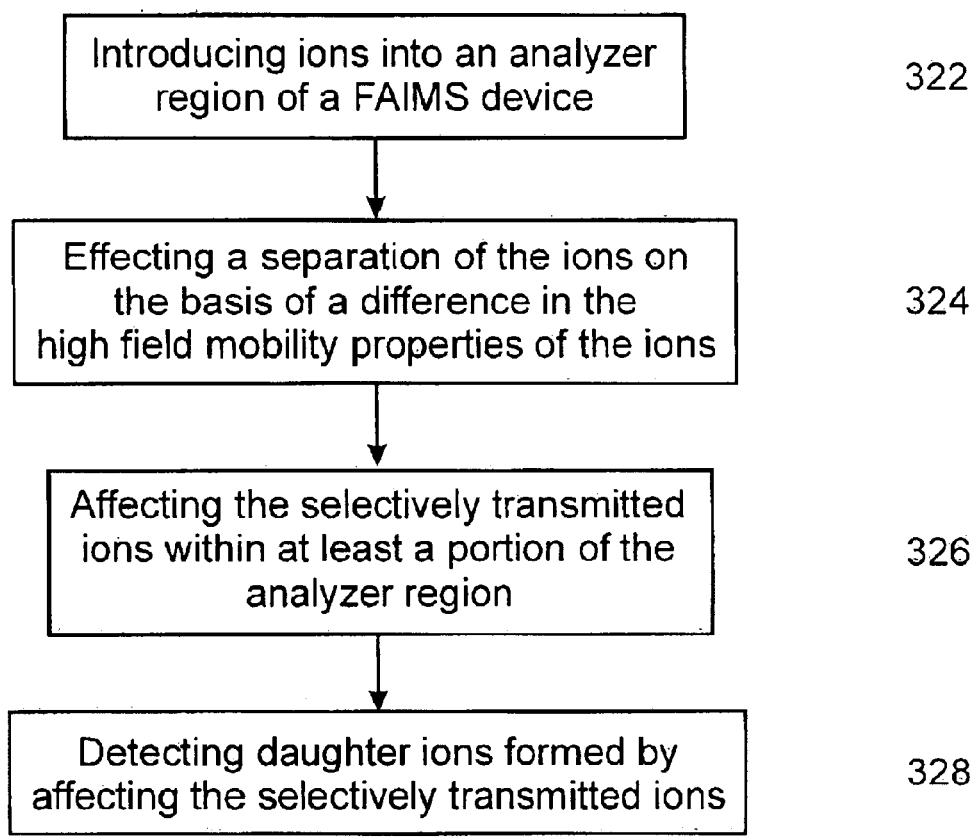
FIG. 12 is a simplified flow diagram for a method of affecting the selectively transmitted ions; and, FIG. 13 is a simplified flow diagram for a method of affecting the selectively transmitted ions.

Referring now to FIG. 12, shown is a simplified flow diagram for a method of affecting the selectively transmitted ions. At step 322, a mixture of ions including an ion type of interest is introduced into a FAIMS analyzer region of, for example, one of the above-mentioned FAIMS devices 30, 61, 90, 120, 160 and 190. Optionally, the ions are produced within the analyzer region from a suitable sample using, for example, a laser-based ionization technique. At step 324, appropriate conditions are provided within the FAIMS analyzer region for effecting a separation of the ions, to selectively transmit the ion type of interest to at least a portion of the analyzer region. At step 326, the ions are affected in order to induce a change therein. For example, a stimulus is provided to the selectively transmitted ions at step 326. Some non-limiting examples of suitable forms of stimuli include: directing an incident beam of infrared light through the at least a portion; directing an incident beam of laser light through the at least a portion; and, applying a strong electric field within the at least a portion. Optionally, a combination including two or more of the above-mentioned stimuli is provided. Changes that are induced by the stimulus include but are not limited to: conformational changes; dissociation of weakly bound molecules; and, chemical bond breakage. Ions formed when the selectively transmitted ions undergo such a change are referred to herein as "daughter ions". At step 328 the daughter ions are detected. Of course, daughter ions may only be detected if they have high field mobility properties that are suitable for transmitting the daughter ions within the FAIMS analyzer region under the ambient conditions of applied CV, applied DV, carrier gas flow rate, etc. Optionally, the daughter ions are detected using one of an optical based detection technique, a mass spectrometric detection technique and electrometric detection.

Figure 13:
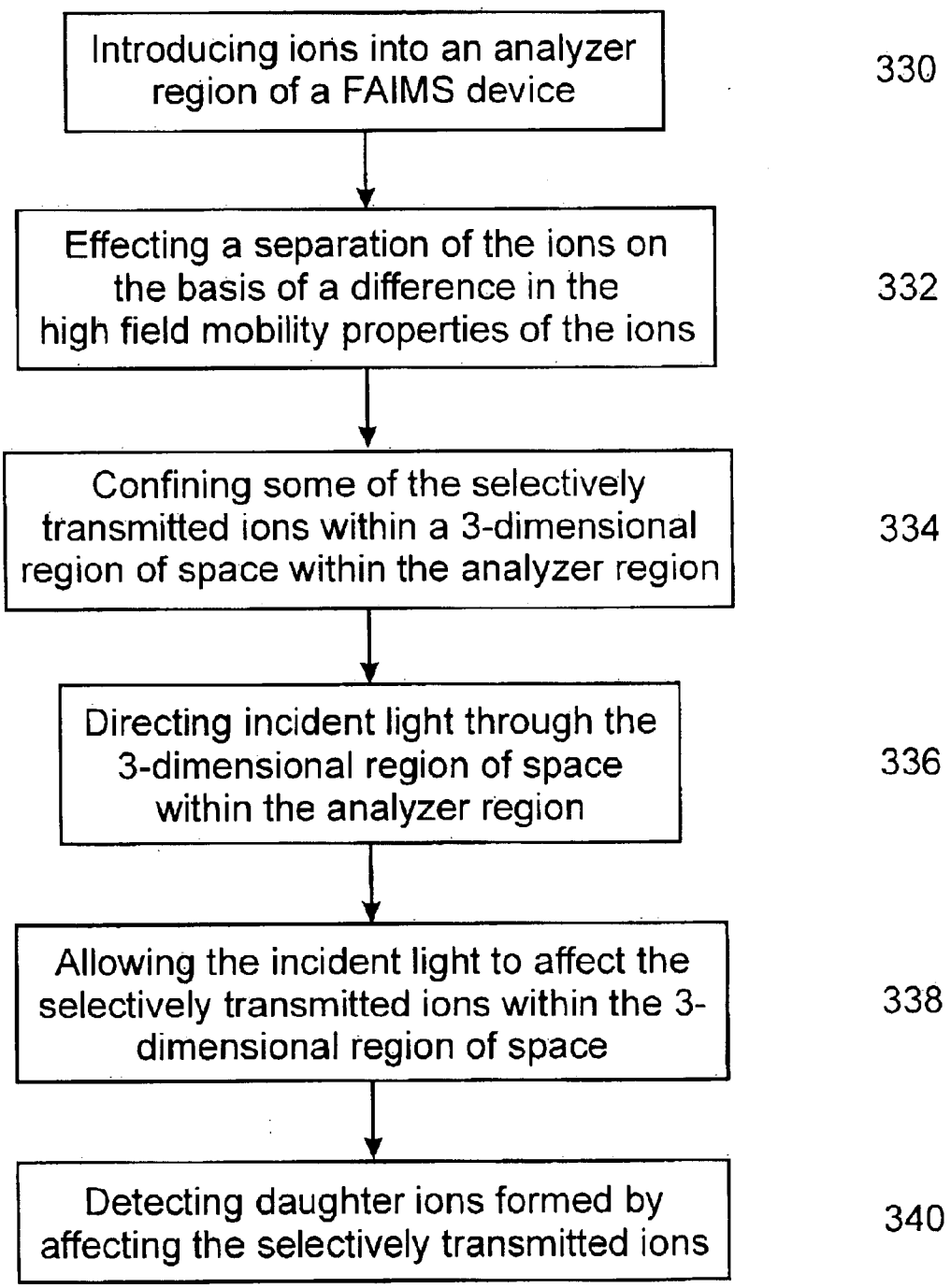

Referring now to FIG. 13, shown is a simplified flow diagram for another method of affecting the selectively transmitted ions. At step 330, a mixture of ions including an ion type of interest is introduced into a FAIMS analyzer region of, for example, one of the above-mentioned FAIMS devices 30, 61, 90 and 120. Optionally, the ions are produced within the analyzer region from a suitable sample using, for example, a laser-based ionization technique. At step 332, appropriate conditions are provided within the FAIMS analyzer region for effecting a separation of the ions, to selectively transmit the ion type of interest to a reaction portion within the analyzer region. At step 334, some of the selectively transmitted ions are confined within a 3-dimensional region of space overlapping with the reaction portion. Confining the selectively transmitted ions within the 3-dimensional region of space results in a higher ion density within the reaction portion of the analyzer region. At step 336, incident light is directed through the 3-dimensional region of space within the analyzer region. For example, light from one of an infrared light source and a laser light source is directed through a first light transmissive optical port in a direction toward the 3-dimensional region of space. At least one of the intensity and the frequency of the incident light is selected to affect the ions within the 3-dimensional region of space. At step 338 the incident light is allowed to interact with the selectively transmitted ions confined within the 3-dimensional region of space, to produce daughter ions. The daughter ions are formed from the selectively transmitted ions as a result of structural changes that include but are not limited to: conformational changes; dissociation of weakly bound molecules; and, chemical bond breakage. The daughter ions are detected at step 340. Of course, daughter ions may only be detected if they have high field mobility properties that are suitable for transmitting the daughter ions within the FAIMS analyzer region under the ambient conditions of applied CV, applied DV, carrier gas flow rate, etc. Optionally, the daughter ions are detected using one of an optical based detection technique, a mass spectrometric detection technique and electrometric detection.

Some non-limiting examples of optional features that may be employed in conjunction with the various embodiments of the instant invention will now be described briefly. The light transmissive window material that is used to form an optical port is optionally one of a light focusing element and a light dispersing element. Further optionally, a reflective surface is provided within the FAIMS analyzer region for directing light that propagates from a light source though an optical port back through the optical port to a detector element. Advantageously, the path length of the light through the gaseous sample is increased and only a single optical port is required.

Numerous other embodiments may be envisaged without departing from the spirit and scope of the invention.

What is claimed is:

1. An apparatus for separating ions in the gas phase, comprising:
    a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting a first type of ion along an average ion flow path within the analyzer region at a given combination of asymmetric waveform voltage and compensation voltage; and,
    an optical port disposed adjacent to a portion of the analyzer region other than a portion including an origin of the average ion flow path, the optical port formed of a light transmissive material other than a gas, which material is transmissive to light within a predetermined range of wavelengths for supporting the propagation of light having a wavelength within the predetermined range of wavelengths between the analyzer region and a region that is external to the analyzer region.

2. An apparatus according to claim 1, wherein the optical port is disposed adjacent to a portion of the analyzer region, the portion of the analyzer region being displaced from an origin of the average ion flow path such that, in use, ions travel a sufficient distance within the analyzer region, between the origin of the average ion flow path and the optical port, for affecting at least a partial separation of a mixture of ion types including the first type of ion and at least a second type of ion.

3. An apparatus according to claim 1, wherein the light transmissive material forms an approximately gas-tight seal with the one of the two electrodes.

4. An apparatus according to claim 1, wherein the region that is external to the analyzer region includes a light detector in optical communication with the optical port for detecting light propagating through the optical port and for providing an electrical signal relating to the detected light.

5. An apparatus according to claim 4, comprising a controller in communication with the detector for receiving the electrical signal therefrom and for controlling a physical characteristic of the system for effecting a change of the type of ions being selectively transmitted through the analyzer region.

6. An apparatus according to claim 1, wherein the region that is external to the analyzer region includes a light source in optical communication with the optical port for providing incident light having a wavelength within a predetermined range of wavelengths to the selectively transmitted ions within the analyzer region.

7. An apparatus according to claim 6, wherein the light source comprises an infrared light emitter.

8. An apparatus according to claim 6, wherein the light source comprises a laser light source.

9. An apparatus according to claim 1, wherein the analyzer region includes an inlet orifice and an outlet orifice for introducing a gas flow between the two electrodes and,
    wherein, in use, at least one of the asymmetric waveform voltage, the compensation voltage and the gas flow are adjustable, so as to confine some of the selectively transmitted ions within a 3-dimensional region of space within the analyzer region.

10. An apparatus according to claim 9, wherein the optical port is disposed within a surface of one of the first and second electrodes at a point that is approximately aligned with the 3-dimensional region of space within the analyzer region.

11. An apparatus according to claim 1, wherein the optical port is disposed within a surface of one of the two electrodes.

12. An apparatus according to claim 11, wherein the two electrodes comprise outer and inner generally cylindrical coaxially aligned electrodes defining a generally annular space therebetween, the annular space forming the analyzer region.

13. An apparatus according to claim 12, wherein the analyzer region includes an inlet orifice and an outlet orifice for introducing a gas flow between the outer and inner generally cylindrical coaxially aligned electrodes and, wherein, in use, at least one of the asymmetric waveform voltage, the compensation voltage and the gas flow are adjustable, so as to confine some of the selectively transmitted ions within a 3-dimensional region of space within the analyzer region.

14. An apparatus according to claim 13, wherein the optical port is disposed within a surface of the outer generally cylindrical electrode at a point along the length of the outer generally cylindrical electrode that is approximately aligned with the 3-dimensional region of space within the analyzer region.

15. An apparatus according to claim 14, wherein the region that is external to the analyzer region includes a light source in optical communication with the optical port for providing incident light having a wavelength within a predetermined range of wavelengths to the selectively transmitted ions within the 3-dimensional region of space within analyzer region.

16. An apparatus according to claim 15, wherein the light source comprises an infrared light emitter.

17. An apparatus according to claim 15, wherein the light source comprises a laser light source.

18. An apparatus according to claim 10, wherein the two electrodes comprise outer and inner generally cylindrical coaxially aligned electrodes defining a generally annular space therebetween, the annular space forming the analyzer region.

19. An apparatus according to claim 18, wherein the inner generally cylindrical electrode includes a curved surface terminus that is shaped for directing the selectively transmitted ions generally radially inwardly toward the ion outlet orifice, the 3-dimensional region of space being located between the curved surface terminus and the ion outlet orifice.

20. An apparatus according to claim 19, wherein the first optical port is disposed within a surface of the outer generally cylindrical electrode.

21. An apparatus according to claim 20, comprising a light detector in optical communication with the first optical port for detecting light propagating through the first optical port and for providing an electrical signal relating to the detected light.

22. An apparatus according to claim 21, comprising a second optical port disposed within the surface of the outer generally cylindrical electrode at a point that lies along the circumference of a cross section taken through the outer generally cylindrical electrode that passes through the first optical port.

23. An apparatus according to claim 22, comprising a light source in optical communication with the second optical port for providing incident light having a wavelength within a predetermined range of wavelengths to the selectively transmitted ions within the analyzer region.

24. An apparatus according to claim 23, wherein the light source comprises an infrared light emitter.

25. An apparatus according to claim 23, wherein the light source comprises a laser light source.

26. An apparatus for separating ions in the gas phase, comprising:
a high field asymmetric waveform ion mobility spectrometer comprising two electrodes defining an analyzer region therebetween, the two electrodes disposed in a spaced apart arrangement for allowing a gas flow to pass therebetween and for providing an electric field within the analyzer region resulting from the application of an asymmetric waveform voltage to at least one of the two electrodes and from the application of a compensation voltage to at least one of the two electrodes, for selectively transmitting a first ion type in the analyzer region at a given combination of asymmetric waveform voltage and compensation voltage, whereby, in use, at least one of the asymmetric waveform voltage, the compensation voltage and the gas flow are adjustable, so as to confine some of the selectively transmitted ions within a 3-dimensional region of space within the analyzer region;

a first optical port disposed within a surface of one of the two electrodes and adjacent to a portion of the analyzer region including the 3-dimensional region of space, the first optical port for propagating incident light along an optical path including the first optical port and the 3-dimensional region of space; and, a second optical port disposed within a surface of one of the two electrodes and adjacent to the portion of the analyzer region including the 3-dimensional region of space, the second optical port for propagating other light, resulting from the passage of the incident light through the 3-dimensional region of space, therethrough.

27. An apparatus according to claim 26, wherein at least one of the first and second optical ports is formed of a light transmissive material other than a gas.

28. An apparatus according to claim 26, comprising a light detector in optical communication with the second optical port, for receiving the other light propagating through the second optical port and for providing an electrical signal relating to the other light.

29. An apparatus for separating ions in the gas phase, comprising:
a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting a first type of ion along an average ion flow path within the analyzer region at a given combination of asymmetric waveform voltage and compensation voltage;

an optical port disposed adjacent to a portion of the analyzer region other than a portion including an origin of the average ion flow path, the optical port formed of a light transmissive material other than a gas, which material is transmissive to light within a predetermined range of wavelengths for supporting the propagation of light having a wavelength within the predetermined range of wavelengths between the analyzer region and a region that is external to the analyzer region;

a light detector disposed external to the analyzer region and in optical communication with the optical port, for detecting light propagating through the optical port and for providing an electrical signal relating to the detected light; and, a controller in communication with the detector for receiving the electrical signal therefrom and for controlling a physical characteristic of the system for effecting a change of the type of ions being selectively transmitted through the analyzer region, wherein the analyzer region includes an inlet orifice and an outlet orifice for introducing a gas flow between the two electrodes, and wherein the physical characteristic of the system is one of the asymmetric waveform voltage, the compensation voltage, a composition of the gas flow and a flow rate of the gas flow.

30. An apparatus for separating ions in the gas phase, comprising:
a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting a first type of ion along an average ion flow path within the analyzer region at a given combination of asymmetric waveform voltage and compensation voltage;

an optical port disposed adjacent to a portion of the analyzer region other than a portion including an origin of the average ion flow path, the optical port formed of a light transmissive material other than a gas, which material is transmissive to light within a predetermined range of wavelengths for supporting the propagation of light having a wavelength within the predetermined range of wavelengths between the analyzer region and a region that is external to the analyzer region; and, a second optical port disposed within a surface of one of the two electrodes and in optical communication with the optical port, such that during use light propagating along an optical path including one of the optical port and the second optical port is directable through the other one of the optical port and the second optical port, wherein the optical port is disposed within a surface of one of the two electrodes.

31. An apparatus according to claim 30, comprising a reflective surface disposed within the optical path for directing light propagating along the optical path.

32. An apparatus for separating ions in the gas phase, comprising:

a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting a first type of ion along an average ion flow path within the analyzer region at a given combination of asymmetric waveform voltage and compensation voltage; and, an optical port disposed adjacent to a portion of the analyzer region other than a portion including an origin of the average ion flow path, the optical port formed of a light transmissive material other than a gas, which material is transmissive to light within a predetermined range of wavelengths for supporting the propagation of light having a wavelength within the predetermined range of wavelengths between the analyzer region and a region that is external to the analyzer region, wherein the optical port comprises a light-focussing element.

33. An apparatus for separating ions in the gas phase, comprising:

a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting a first type of ion along an average ion flow path within the analyzer region at a given combination of asymmetric waveform voltage and compensation voltage; and, an optical port disposed adjacent to a portion of the analyzer region other than a portion including an origin of the average ion flow path, the optical port formed of a light transmissive material other than a gas, which material is transmissive to light within a predetermined range of wavelengths for supporting the propagation of light having a wavelength within the predetermined range of wavelengths between the analyzer region and a region that is external to the analyzer region, wherein the optical port comprises a light-dispersing element.

* * * * *